United States Patent [19]
Portnoy et al.

[11] Patent Number: 5,830,702
[45] Date of Patent: Nov. 3, 1998

[54] **LIVE, RECOMBINANT *LISTERIA MONOCYTOGENES* AND PRODUCTION OF CYTOTOXIC T-CELL RESPONSE**

[75] Inventors: Daniel A. Portnoy; Yvonne Paterson, both of Philadelphia, Pa.

[73] Assignee: The Trustees of the University of Pennsylvania, Philadelphia, Pa.

[21] Appl. No.: 366,477

[22] Filed: Dec. 30, 1994

Related U.S. Application Data

[63] Continuation of Ser. No. 192,857, Feb. 7, 1994, abandoned, which is a continuation of Ser. No. 38,356, Mar. 26, 1993, abandoned, which is a continuation-in-part of Ser. No. 606,546, Oct. 31, 1990, abandoned.

[51] Int. Cl.$^6$ .......................... C07H 21/04; C12N 15/63; A61K 39/00; C12P 21/06

[52] U.S. Cl. .................. 435/69.3; 424/200.1; 424/185.1; 424/197.1; 424/210.1; 424/192.1; 424/184.1; 424/209.1; 435/69.7; 435/172.3; 435/822; 435/320.1; 536/23.1; 536/23.4; 536/23.72; 514/2; 935/27; 935/23

[58] Field of Search .............................. 424/200.1, 184.1, 424/185.1, 197.1, 210.1, 192.1, 209.1; 435/69.3, 69.7, 172.3, 822, 320.1; 536/23.1, 23.4, 23.72; 514/2; 935/27, 23

[56] References Cited

U.S. PATENT DOCUMENTS

| | | | |
|---|---|---|---|
| 4,816,253 | 3/1989 | Likhite et al. ............................ | 424/92 |
| 4,945,050 | 7/1990 | Sanford et al. ....................... | 435/172.1 |

FOREIGN PATENT DOCUMENTS

| | | |
|---|---|---|
| 9315212 | 8/1993 | WIPO . |

OTHER PUBLICATIONS

Barry et al., "Pathogenicity and Immunogenicity of *Listeria Monocytogenes* Small–Plaque Mutants Defective for Intracellular Growth and Cell–to–Cell Spread", *Infec. Immun.* 1992, 60, 1625–1632.

Berche et al., "Intracellular Growth of *Listeria monocytogenes* as a Prerequisite for in vivo Induction of T Cell–Mediated Immunity", *J. Immunol.* 1987, 138, 2266–2271.

Bielecki, et al, "*Bacillus subtilis* Expressing a Hemolysin Gene From *Listeria monocytogenes* Can Grow in Mammalian Cells", *Nature* 1990, 345, 175–176.

Brown, T. et al., "An attenuated aroA *salmonella typhimurium* vaccine elicits humoral and cellular immunity to cloned β–galactosidase in mice", *J. of Infectious Diseases* 1987, 155(1), 86–92.

Camilli, et al., "Intracellular Methicillin Selection of *Listeria monocytogenes* Mutants Unable to replicate in a Macrophage Cell Line", *PNAS USA* 1989, 86, 5522–5526.

Carbone et al., "Class I –Restricted Processing and Presentation of Exogenous Cell–Associated Antigen In Vivo", *J. Exp. Med.* 1990, 171, 377.

Cossart et al., "Listeriolysin O Is Essential for Virulence of *Listeria Monocytogenes:* Direct Evidence Obtained by Gene Complementation", Infection and Immunity 57:3629–3636 (1989).

Flamm, et al., "Introduction of pAMβ1 into *Listeria Monocytogenes* by Conjugation and Homology Between Native *L. Monocytogenes* Plasmids", Infection and Immunity 44:157–161 (1984).

Gaillard, et al., "Transposon Mutagenesis as a Tool to Study the Role of Hemolysin in the Virulence of *Listeria Monocytogenes* ", Infection and Immunology 52:50–55 (1986).

Gawron–Burke, C. and Clewell, D.B., "Regeneration of Insertioanlly Inactive Streptococcal DNA Fragments After Excision of Transposon Tn916 in *Escherichia Coli:* Strategy for Targeting and Cloning of Genes from Gram–Positive Bacteria", Journal of Bacteriology 159:214–221 (1984).

Kathariou, S. et al., "Tn916–induced mutations in the hemolysin determinant affecting virulence of *listeria monocytogenes*", *J. of Bacteriology* 1987, 169(3), 1291–1297.

Kingdon, G.C and Sword, C.P., "Biochemical and immunological effects of *listeria monocytogenes* hemolysin", *Infection and Immunity* 1970, 1(4), 363–372.

Mengaud et al, Expression in *Escherichia coli* and Sequence Analysis of the Listeriolysin O Determinant of *Listeria Monocytogenes'*, *Infect. Immun.* 1988, 56, 766–772.

Portnoy et al., "Role of Hemolysin for the Intracellular Growth of *Listeria monocytogenes*", *J. Exp. Med.* 1988, 176, 1459–1471.

Portnoy et al., "γ Interferon Limits Access of *Listeria Monocytogenes* to the Macrophage Cytoplasm ", *J. Exp. Med.* 1989, 170, 2141–2146.

Ralph et al., "Reticulum Cell Sarcoma: An Effector Cell in Antibody–Dependent Cell–Mediated Immunity", *J. Immun.* 1975, 114, 898.

Tilney et al, "Actin Filaments and the Growth, Movement, and Spread of the Intracellular Bacterial Parasite, *Listeria monocytogenes*", *J. Cell. Biol.* 1989, 109, 1597–1608.

Youngman, "Plasmid Vectors for Recovering and Exploiting Transpositions in Bacillus and Other Gram–Positives", 1987, pp. 79–103, in K. Hardy (ed.), Plasmids. A Practical Approach, IRL Press, Oxford.

Bodmer, H. et al., "Enhanced recognition of a modified peptide antigen by cytotoxic T cells specific for influenza nucleoprotein", *Cell* 1988, 52, 253–258.

(List continued on next page.)

*Primary Examiner*—N. M. Minnifield
*Attorney, Agent, or Firm*—Woodcock Washburn Kurtz Mackiewicz & Norris LLP

[57] ABSTRACT

Vaccines comprising an attenuated strain of Listeria spp. expressing a selected foreign antigen and methods of eliciting protective immunity by administering an effective amount of the vaccine are provided. The vaccines of the present invention are designed specifically to elicit strong cell-mediated immunity, and are particularly useful for protection in infections which can apparently persist and spread in the presence of neutralizing antibodies invoked by humoral immunity.

15 Claims, 8 Drawing Sheets

OTHER PUBLICATIONS

Bouwer, H. et al., "Listeriolysin O is a target of the immune response to *listeria monocytogenes*", *J. of Experimental Medicine* 1992, 175, 1467–1471.

Camilli et al., "Insertional Mutagenesis of *Listeria monocytogenes* with a Novel Tn917 Derivative That Allows Direct Cloning of DNA Flanking Transposon Insertions", J. of Bacteriology 172:3738–3744 (1990).

Davis et al, *Microbiology*, Third Edition, 1980, pp. 503, 854, Harper & Row.

Del Val et al., "Efficient Processing of an Antigenic Sequence for Presentation by MHC Class I Molecules Depends on Its Neighboring Residues in the Protein", Cell 66:1145–1153 (1991).

Eisenlohr, et al., "Flanking Sequences Influence the Presentation of an Endogenously Synthesized Peptide to Cytotoxic T Lymphocytes", The Journal of Experimental Medicine 175:481–487 (1992).

Gaillard et al, "In Vitro model of Penetration and Intracellular Growth of *Listeria monocytgenes* in the Human Enterocyte–Like Cell Line Caco–2", *Infect. Immun.* 1987, 55, 2822–2829.

Lamb, R.A., "The Influenza Virus RNA Segments and Their Encoded Proteins", Genetics of Influenz Viruses, Palese and Kingsbury, eds., pp. 21–69, Springer Verlag, Vienna, New York.

Hahn et al, "Presentation of Viral Antigen to Class I Major Histocompatibility Comoplex–restricted Cytotoxic T Lymphocyte. Recognition of an Immunodominant Influenza Hemaglutinin Site by Cytotoxic T Lymphocyte Is Independent of the Position of the Site", *J. Exp. Med.* 1991, 174, 733–736.

Koga et al, "Induction by Killed *Listeria monocytogenes* of Effector T Cells Mediating Delayed–type Hypersensitivity but not Protection in mice", *Immunology* 1987, 62, 241–248.

Kuhn et al, "Hemolysin Support Survival but not Entry of the Intracellularl Bacterium *Listeria monocytogenes*", *Infect. Immun.* 1988, 56, 79–82.

Mengaud et al, "Transcriptional mapping and Nucleotide Sequence of the *Listeria monocytognes* hlyA Region Reveal Structural Features That May be Involved in regulation", *Infect. Immun.* 1989, 57, 3695–3701.

Miller et al, "Constitutive Expression of the PhoP regulon Attenuates Salmonella Virulence and Survival Within Macrophanges", *J. Bacteriol.* 1990, 172, 2485–2490.

Pamer et al., "Precise Prediciton of a Dominant Class I MCH–Restricted Epitope of *Listeria monocytogenes*", *Nature* 1991, 353, 852–855.

Portnoy et al., "Molecular Determinant of *Listeria monocytogenes* Pathogenesis", *Infect. and Immun.* 1992, 60, 1263–1267.

Ratner et al., "Complete Nucleotide Sequence of the AIDS virus, HTLV–III", *Nature* 1985, 313(1), 277–284.

Schafer, Rosana et al., "Induction of a Cellular Immune Response to a Foreign Antigen by a Recombinant *Listeria Monocytogenes* Vaccine" J. of Immunology 149: 53–59 (1992).

Stover et al., "New use of BCG for recombinant vaccines", Nature 351:456–460 (1991).

Sun et al., "Isolation of *Listeria monocytogenes* Small–Plaque Mutants Defective for Intracellular Growth and Cell–to–Cell Spread", Infection and Immunity 58:3770–3778 (1990).

Moore et al., "Introduction of Soluble Protein into the Class I Pathway of Antigen Processing and Presentation", Cell 1988, 54, 777–785.

Trieu–Cuot et al, "Shuttle Vectors Containing a Multiple Cloning Site and a lacZ x Gene for Conjugal transfer of DNA From *Eshcerichia COli* to Gram–positive Bacteria", *Gene* 1991, 102, 99–104.

Wirth et al, "Highly Efficient Protoplast Transformation System for *Streptococcus faecalis* and a New *Escherichia coli–S. faecalis* Shuttle Vector", *J. Bacteriol.* 1986, 165, 831–836.

Wuenscher et al., "Gene Disruption by Plasmid Integration in *Listeria monocytogenes:* Insertional Inactivation of the Listeriolysin Determinant lisA", *Mol. Gen. Genet.,* 1991, 228, 177–182.

Ikonomidis, G. et al., "Delivery of a Viral Antigen to the Class I Processing and Presentation Pathway by *Listeria monocytogenes*", *J. Exp. Med.* 1994, 180, 2209–2218.

Schafer, R. et al., "Induction of a Cellular Immune Response To a Foreign Antigen by a Recombinant *Listeria monocytogenes* Vaccine", *The J. of Immunology* 1992, 149, 53–59.

Schafer et al. 1992. J. Immunol. 149(1):53–59.

Barry et al. 1992. Infect Imm. 60(4):1625–32.

Connell et al. 1992. Current Opinion Immunol. 4:442–48.

Trieu–Cuot. et al. 1991. Genes. 102:99–104.

Schafer et al. 1992. J. Cell. Biochem. Suppl. 0(16 Part D):70 Abs #447.

Camilli et al. 1989 PNAS USA 86:5522–26.

Berche et al. 1987. J. Immunol. 138:2266–2271.

Brown et al. 988 J. Infect. Dis. 155(1):86–92.

Charoenvit et al. 1991. Science 251:668–671.

Cox. 1991. TIB TECH. 9:389–394.

Hoffman et al. 1987. Science 237:639–642.

Hoffman et al. 1993. Mol. Immunological Considerations in Mal. Vaccine Dev. ed. Good & Saul. pp. 149–167.

Haynes. 1993. Science 260:1279–1286.

Shen et al, 1995, PNAS 92(9):3987–3991.

Sheehan et al, 1995, J. Bacteriol. 177(22):6469–76.

DeLibero et al, 1986, J. Immunol. 137(8):2688–2694.

Ikonomidis. 1996. Dissertation Abs. Int'l. 57(4B) p. 2462 Abstract only.

Wilson et al, 1995. Am. J. Trop. Med. Hyg. 53(2) Suppl:132 Abstract only.

Ikonomidis et al, 1995, Vaccines 95 pp. 317–326.

Pan et al 1995, Nature Medicine. 1(5):471–477.

Loessner et al, 1996 Applied & Environmental Microbiol 62(8):3057–3060.

Hess et al, 1996 PNAS 93(4):1458–63.

Frankel et al, 1995, J. Immunol 155:4775–82.

Goosens et al 1995, Intl Immunol. 7(5):797–805.

Tite et al, 1990, Immunology 70:540–546.

Gao et al 1992, Inf. & Imm. 60(9):3780–3789.

Brett et al 1993, J. Immunol. 150:2869–2884.

LIVE, RECOMBINANT *LISTERIA MONOCYTOGENES* AND PRODUCTION OF CYTOTOXIC T-CELL RESPONSE

This is a continuation of application Ser. No. 08/192,857, filed Feb. 7, 1994, which is a continuation of application Ser. No. 08/038,356, filed Mar. 26, 1993, abandoned, which was a continuation-in-part application of application Ser. No. 07/606,546, filed Oct. 31, 1990.

BACKGROUND OF THE INVENTION

*Listeria monocytogenes* is a Gram-positive, food-borne human and animal pathogen responsible for serious infections in immunocompromised individuals and pregnant women. Severe L. monocytogenes infections in humans are characterized by meningitis, meningoencephalitis, septicemia, and fetal death. L. monocytogenes is ubiquitous in nature and, in addition, can be isolated from a wide variety of warm blooded animals.

L. monocytogenes enters the host cytoplasm and uses a host system of actin-based motility to mediate movement both within a cell and from cell-to-cell without leaving the cytoplasm. The intracellular parasitism of L. monocytogenes can be broadly divided into five stages, including (i) internalization, (ii) escape from a host vacuole, (iii) intracellular growth, (iv) intracellular movement and pseudopod formation using host actin filaments, and (v) cell-to-cell spread which proceeds through an intermediate double-membraned vacuole.

More specifically, subsequent to internalization, L. monocytogenes escapes from a host vacuole, an event mediated, at least in part, by the action of a pore-forming hemolysin, Listeriolysin O. Next, rapid cell division ensues and the bacteria become encapsulated by short actin filaments and other actin binding proteins. The actin based structure is rearranged to form a long tail behind the bacteria which appears to mediate movement of the bacteria through the cytoplasm to the cell periphery. Next, some of the bacteria are presented in pseudopod-like structures which are apparently recognized and internalized by neighboring cells. Thus, within the cytoplasm of the second cell, the bacteria are found surrounded by a double membrane. Both membranes are solubilized and the cycle is repeated. In this way, the bacteria spread from one cell to another without ever leaving the cytoplasm thereby providing an explanation for the absolute requirement of cell mediated immunity and the observation that antibodies are not protective. Thus, once inside a host cell, infecting *Listeria monocytogenes* and their progeny can spread from cell to cell by remaining intracellular, bypassing the humoral immune system of the host organism. Further, data suggest that actin filaments are essential for the spread of L. monocytogenes from cell to cell. Tilney and Portnoy, *J. Cell. Biol.* 1989, 109, 1597–1608.

Several bacterial genes whose products are required for these processes have recently been identified using transposon mutagenesis and characterization of the resulting defects in tissue-culture models of infection. One region of the L. monocytogenes genome encodes a number of these virulence factors, including a pore-forming hemolysin, Listeriolysin O (LLO), which is largely responsible for lysis of the initial vacuole; two distinct phospholipases C including one, PI-PLC, specific for phosphatidylinositol and the other, PC-PLC, having a broad substrate specificity that includes phosphatidylcholine (PC); a metalloprotease, Mpl, which apparently can activate PC-PLC; ActA, a surface protein required for actin assembly; and lastly, PrfA, which appears to be a specific transcription factor required for the regulated expression of genes for the above-mentioned proteins.

It has been suggested that the process of bacterial growth inside macrophages is required to initiate the expression of T cell-mediated immunity; the presence of viable *Listeria monocytogenes* at a significant level in a host is not sufficient per se to induce detectable T cell clonal expansion. Berche et al., *J. Immunol.* 1987, 138, 2266–2271.

An important obstacle to the development of efficient vaccines against intracellular parasites is the difficulty of inducing in vivo T cell-mediated immunity with dead microorganisms as well as with crude or purified extracts of the prior art. This contrasts with the facility of immunization with low sublethal doses of viable microorganisms. Therefore, the step of T-cell induction is crucial to the development of an effective vaccine. There is evidence that acquired resistance against L. monocytogenes depends upon the generation of specific T-cells capable of activating and recruiting bone marrow-originated macrophages in infectious foci, which ultimately destroy bacteria. Further, it has been demonstrated that clonal expansion of specific T-cells requires a phase of antigen handling by macrophages, initiating a process of recognition by specific T-cells of L. monocytogenes antigens. For example, see Berche et al., *J. Immunol.* 1987, 138, 2266–2271.

Thus, there remains an unmet need for live vaccines capable of causing the production of the cytotoxic T-cell response in a vertebrate against a foreign pathogen. The present invention meets this need, for example, through providing genetically engineered Listeria spp. expressing foreign antigen.

The live vaccines of the present invention invade host cells, delivering the foreign antigen into the cytoplasm, thus invoking the cytotoxic T-cell response.

SUMMARY OF THE INVENTION

In contrast to other recombinant vaccines that are under development, Listeria spp. such as *Listeria monocytogenes* provide advantages that include the ability to break down the vacuole within the host cell and enter the host cytoplasm, thus generating a stronger cytotoxic T-cell response. Other advantages include lesser virulence, the lack of production of an endotoxin, and a more suitable response to a wide range of antibiotics.

The vaccines of the present invention comprise selected attenuated mutants of Listeria spp., preferably *Listeria monocytogenes*, expressing foreign antigens. In accordance with the present invention, Listeria spp. can be genetically engineered to express a foreign antigen in the cytoplasm of infected macrophages and other non-phagocytic cells such as hepatocytes and epithelial cells. The foreign antigen need not be secreted by Listeria spp., although in preferred embodiments, the antigen is secreted.

Recombinant antigens which will be recognized by the cell-mediated arm of the immune system are preferred. Subsequent T-cell responses may then be directed toward any cell that displays the foreign antigen.

The growth of the Listeria spp. within the host cell is required to initiate in vivo expression of T-cell mediated immunity, and thus live vaccines may succeed in infections where heat-killed vaccines would be ineffective. Further, live attenuated pathogens elicit a longer-lasting immunity. T-cell immunity is especially important in diseases in which a humoral response is ineffective. The vaccines of the present invention, designed specifically to elicit substantial cell-mediated immunity, may be thus particularly effective in protection from or treating diseases such as malaria and HIV infection which can apparently persist and spread in the presence of neutralizing antibodies invoked by humoral immunity.

In one embodiment of the invention, a Listerial vaccine against influenza demonstrated that the vaccine generates a CTL response against the influenza antigen expressed by genetically engineered Listeria monocytogenes. Given the present disclosure, one skilled in the art will be able to create Listeria-based vaccines against a number of diseases in order to generate a cytotoxic T-cell response.

BRIEF DESCRIPTION OF THE DRAWINGS

FIG. 1A represents chromosomal integration of pDP1526 by homologous recombination between the ΔplcA allele on the plasmid, which had the internal NsiI (N) to PstI (P) fragment deleted and the wild-type plcA chromosomal allele. The designated cross-over points are arbitrary however, recombination may occur on either side of the internal deletion. FIG. 1B represents the resulting integration structure on the chromosome which was selected for by growth at a non-permissive temperature for plasmid replication in the presence of chloramphenicol. Upon passage of the merodiploid intermediate strains for several generations without selective pressure, spontaneous excision of the integrated plasmid from the chromosome occurred (FIG. 1C). After curing of the excised plasmid at a non-permissive temperature for plasmid replication (FIG. 1D). L. monocytogenes $Cm^S$ revertants were recovered at a frequency of =1%. Approximately 50% of the $Cm^S$ revertants retained the ΔplcA allele on the chromosome. These resulted from excision of the integrated plasmid via homologous recombination on the opposite side of the deletion allele as shown in (FIG. 1C).

FIG. 2 illustrates the generation of a β-galactosidase-specific CTL.

(FIG. 3A) or orally (FIG. 3B) with live L. monocytogenes 10403S or with L. monocytogenes DP-L967, or i.p. with HKLM (heat killed L. monocytogenes) 10403S or HKLM DP-L967 (FIG. 3C), and restimulated in vitro from 2 to 4 weeks. Oral immunizations were with one dose of L. monocytogenes, and mice immunized i.p. received two doses. Specific lysis of cells from 10403S-immunized mice against P815 (■) or P13.1 (dark shading) and of cells from DP-L967-immunized mice against P815 (medium shading) or P13.1 (light shading) was measured in a 4-h $^{51}$Cr release assay. Data shown are for an E:T (effector:target) ratio of 12:1. (*) indicates that the cells had died by week 4.

Figure 1A:
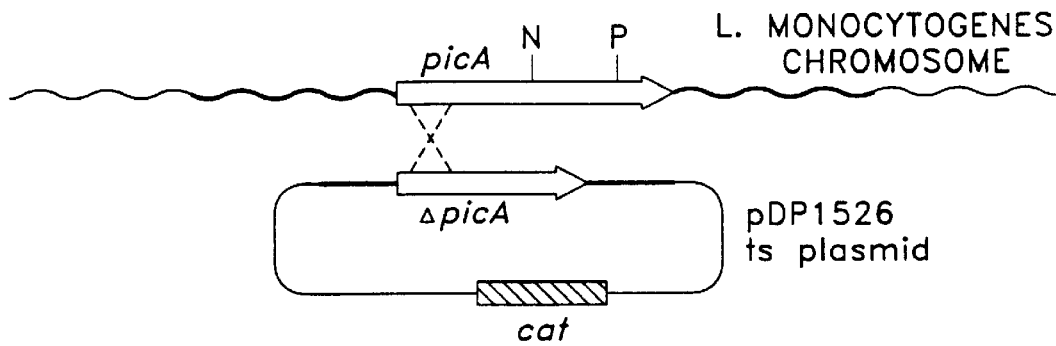
FIGS. 1A, 1B, 1C and 1D are schematic diagrams for construction of the isogenic strains DP-L1552 and DP-L1553 each containing an internal deletion in plcA.
Figure 1B:
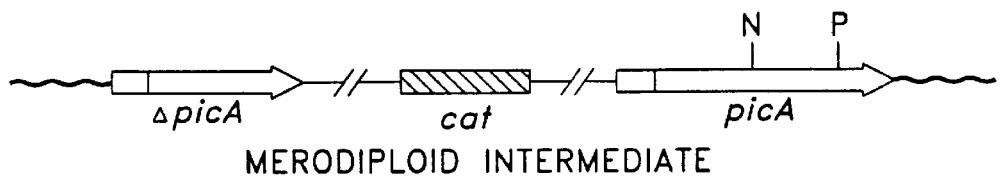
Figure 1C:
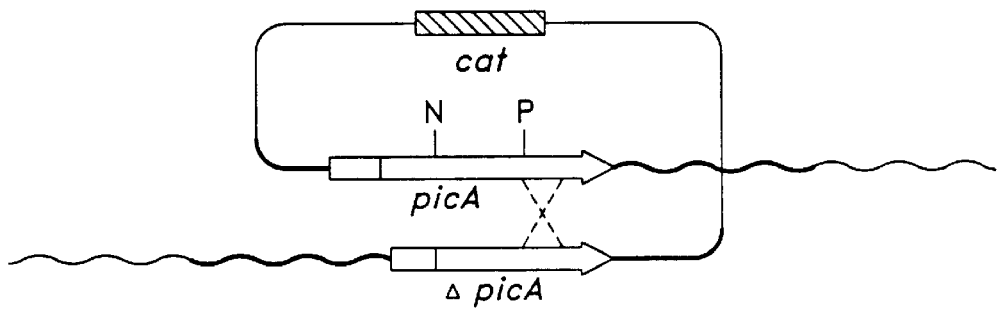
Figure 1D:
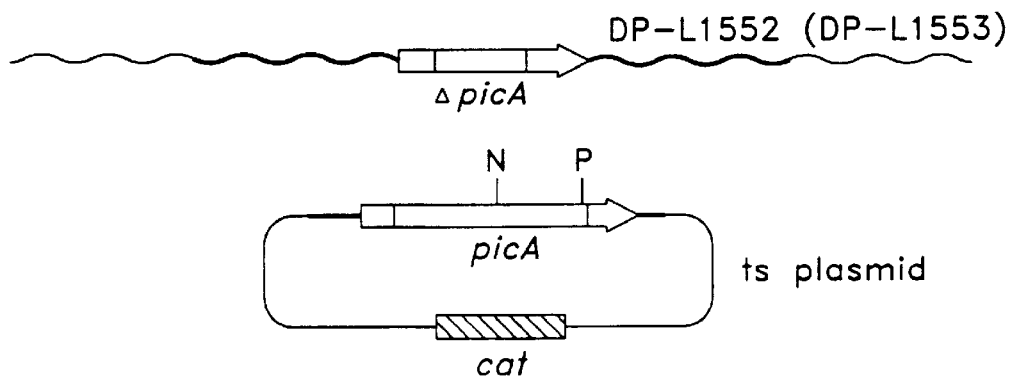

Lane 1 represents an immunoblot of the proteins secreted by L. monocytogenes DP-L2027. This strain is the wild-type strain containing plasmid pAM401-hly-np, prfA. The fusion protein is 105-kDa consisting of 416 amino acids of Listeriolysin O (LLO) and the entire coding sequence of NP (513 amino acids).

Lane 2 represents an immunoblot of the proteins secreted by L. monocytogenes DP-L2028. Same plasmid as in lane 1 but in strain DP-L1075 which has a transposon Tn917-LTV3 in the prfA gene.

Lane 3 represents an immunoblot of the proteins secreted by DP-L1669, a wild-type strain containing pAM401 with a clone which encodes a fusion protein with 416 amino acids of LLO and the first 180 amino acids of NP.

Lane 4 represents an immunoblot of the proteins secreted by DP-L1659, a wild-type strain expressing the 105-kDa fusion. This strain differs from the strain represented by lane 1 in that the plasmid does not contain prfA.

Lane 5 represents an immunoblot of the proteins secreted by DP-L1075, which is the prfA mutant alone. Note it does not secrete detectable LLO.

Lane 6 represents an immunoblot of the proteins secreted by strain 10403S, the wild-type strain.

DETAILED DESCRIPTION OF THE INVENTION

The present invention comprises vaccines using attenuated strains of Listeria spp. expressing a selected foreign antigen. A foreign antigen is defined as an antigenic protein or peptide that substantially corresponds to an antigen derived from an infectious organism such as a virus or bacteria. An antigenic peptide is a portion of a pathogenic protein that is processed and presented to cytotoxic T-cells. The foreign antigen expressed by Listeria spp. need not precisely match the antigen derived from the infectious organism so long as it results in a cytotoxic T-cell response that recognizes the antigenic peptide presented upon infection. The foreign antigen to be targeted may be selected using the knowledge of one skilled in the art, and many antigenic proteins are currently known, such as the NP protein of influenza virus and the gag protein of HIV. Listeria spp. expressing a foreign antigen are those live organisms genetically engineered to produce a foreign antigen.

It is believed that any Listeria species capable of producing infectious disease, and preferably producing hemolysin, can be genetically attenuated according to the methods of the present invention to yield a useful and safe vaccine. Thus, the use of L. monocytogenes in generating attenuated mutants for the vaccines of the present invention may be substituted by other suitable Listeria species to generate similar attenuated mutants. Preferably, the species is L. monocytogenes.

The methods disclosed herein also provide for the selection of novel attenuated mutants useful for vaccines. By attenuation, as used herein, it is meant that the pathogenic characteristics of the Listeria spp. (that is, the ability of the Listeria spp. to cause disease) have been lessened, although the Listeria spp. is alive. Using, for example, intravenous inoculation of Balb/c mice, the $LD_{50}$ is preferably increased above wild-type by at least about 10-fold, more preferably at least about 100-fold, more preferably at least about 1,000-fold, more preferably at least about 10,000-fold, and most preferably at least about 100,000-fold.

Attenuated mutants are for example, a mutant defective for cell-to-cell spread, a mutant partially defective for intracellular growth and cell-to-cell spread, a mutant defective for intracellular growth, an actA negative mutant, and mutants that are defective in at least one phospholipase gene, such as a phospholipase negative mutant, and a double phospholipase negative mutant. Certain nutritional auxotrophs may be less preferred in L. monocytogenes as attenuated mutants since they may not be as easily attenuated.

According to the present invention, an attenuated Listeria spp. mutant is genetically engineered to express a foreign antigen. It is believed that this invention represents the first demonstration of the ability of Listeria spp. to secrete a foreign protein. The introduction of the foreign antigen may occur, for example, through creating a recombinant Listeria spp. in which the DNA encoding the foreign antigen is harbored on a vector. Alternatively, the DNA encoding the foreign antigen may be stably integrated into the Listeria spp. chromosome.

Several approaches may be taken to express the foreign antigen in Listeria spp., as will be understood by one skilled in the art once armed with the present disclosure. One strategy, for example, is to generate a fusion protein of a selected foreign antigen and a Listerial protein. In certain preferred embodiments, the Listerial protein is an enzyme which is involved in lysis of host vacuoles, such as Listeriolysin O or PI-PLC.

Another way in which a foreign antigen may be expressed is through the use of a signal sequence, such as a Listerial signal sequence, for example, the hemolysin signal sequence. Alternatively, for example, foreign genes can be expressed downstream from a L. monocytogenes promoter without creating a fusion protein. Such promoters include, for example, the hly promoter and the actA promoter, as well as others described below. Preferably, the regulatory sequences promote expression of proteins, for example, that are necessary for L. monocytogenes to spread from cell to cell. Such promoters would cause the foreign antigen to be expressed at an appropriate stage of L. monocytogenes infection so that the antigen is properly presented to the host cellular immune system. The antigen made in accordance with the teachings of the present invention may thus be expressed by L. monocytogenes and recognized by the cell-mediated arm of the immune system.

The promoters of various L. monocytogenes genes may be used to express a foreign antigen. In addition, these genes may be used to generate fusion proteins with foreign antigens. L. monocytogenes genes include, for example, plcA, which encodes a phospatidylinositol-specific phospholipase (PI-PLC), mpl, which encodes a metalloprotease, actA, which encodes a surface protein necessary for L. monocytogenes actin assembly, and plcB, which encodes a phospholipase C. Other L. monocytogenes genes include, for example, prfA, which encodes a positive regulatory factor for hly, and inlA, which encodes internalin, a membrane protein. For a review of genes involved in L. monocytogenes pathogenesis, see Portnoy et al., *Infect. and Immun.* 1992 60, 1263–1267.

Preferred embodiments of the present invention are vaccines comprising a selected attenuated strain of L. monocytogenes expressing a foreign antigen capable of causing the production of a cell-mediated immune response. The foreign antigen may comprise, for example, an HIV antigen, a malarial antigen, or an influenza antigen, such as influenza nuclear protein.

A cytotoxic T-cell response is defined as the generation of cytotoxic T-cells capable of detectably lysing cells presenting the foreign antigen. It will be understood by one skilled in the art that the test used in the present disclosure to evaluate cytotoxicity involves determining the total number of stimulated spleen cells as the number of effector cells, only some of which are actually cytotoxic T-cells. Thus, it will be understood that this method of calculating the percentage of cell lysis actually corresponds to a larger percentage of cell lysis due to the nature of the stimulated spleen cells.

In preferred embodiments, at an effector:target ratio of about 50:1, for example, the calculated percentage of cell lysis is preferably at least about 10% above the background level of lysis, the background level being the amount of lysis of cells that do not present the foreign antigen. More preferably, the percentage of cell lysis is at least about 20% above background; more preferably, at least about 40%; more preferably, at least about 60%; and most preferably at least about 70%. A higher percentage of lysis at a lower effector:target ratio is most preferred.

The present invention also provides methods for eliciting a cytotoxic T-cell response to a selected infection in a vertebrate comprising administering an effective amount of a vaccine using Listeria spp., preferably L. monocytogenes, expressing a foreign antigen. Preferably, the foreign antigen comprises a peptide recognized by the cytotoxic T-cells after vaccination and the peptide is substantially the same as an antigenic peptide recognized by the cytotoxic T-cells from an infected vertebrate. It will be understood by one skilled in the art once armed with the present disclosure that a humoral response may also be generated, although it may not be as strong as the cellular response.

The present invention further provides expression vehicles for Listeria spp., and preferably L. monocytogenes, for expressing a fusion protein comprising DNA encoding a Listerial protein in translational reading frame with DNA encoding a foreign antigen, wherein the fusion protein is secreted by Listeria spp. Preferably, the expression vehicle is substantially retained in Listeria spp. upon infection of a vertebrate. Additionally, the present invention provides Listeria spp. cultures capable of expressing and secreting a fusion protein, comprising viable Listeria spp. transformed with an expression vehicle containing DNA encoding at least a portion of a Listerial protein in translational reading frame with DNA encoding a foreign antigen.

The vaccines of the present invention are administered to a vertebrate by contacting the vertebrate with a sublethal dose of the genetically engineered Listeria spp. The Listeria vaccine may be administered orally, for example. Oral administration is preferred; the efficacy of this mode of administration in generating a cytotoxic T-cell response has been demonstrated in Examples 3 and 4 below. The total amount to be administered will depend on the size, nature and weight of the vertebrate to be vaccinated.

The attenuated L. monocytogenes strains of the invention are capable of normal invasion of a host cell, but incapable of normal survival or growth in the cell or cell-to-cell spread. In accordance with the present invention, it is believed that in order for a microbe to be pathogenic, it must be capable of (i) associating with a target host cell (cell recognition), (ii) invading the target host cell, (iii) surviving and growing intracellularly in the target host cell, and (iv) disseminating from host cell to other sites (colonize other distal sites). By disrupting the ability of the L. monocytogenes to survive and/or grow intracellularly, its pathogenic characteristics (the ability of the L. monocytogenes to cause disease) have been significantly lessened. By being capable of normal invasion of a host cell (that is, being able to enter the host cell), however, L. monocytogenes is able to elicit a cellular (T-cell) immunogenic response. Thus, in contrast to dead L. monocytogenes organisms, such as those of Likhite et al., U.S. Pat. No. 4,816,253, the vaccines of the present invention involve live, attenuated L. monocytogenes that are capable of generating a cytotoxic T-cell response.

In accordance with the invention, the attenuated Listeria spp. strain may be employed, in combination with a pharmaceutically acceptable diluent, as a vaccine composition, useful in immunizing a patient against infection from a selected organism, such as influenza virus, Plasmodium species such as Plasmodium falciparum, and HIV. Immunizing a patient means providing the patient with at least some degree of immunity against selected pathogens.

Further, the vaccines of the present invention may be used for treatment post-exposure. In general, the use of vaccines for post-exposure treatment would be recognized by one skilled in the art, for example, in the treatment of rabies and tetanus. The same vaccine of the present invention may be used, for example, both for immunization and to boost immunity after exposure. Alternatively, a different vaccine of the present invention may be used for post-exposure treatment, for example, such as one that is specific for antigens expressed in later stages of exposure.

Any one of a number of well known pharmaceutically acceptable diluents may be employed in the vaccines of the invention. Suitable diluents include, for example, sterile, distilled water, saline, phosphate buffered solution, and the like. The amount of the diluent may vary widely, as those skilled in the art will recognize.

In accordance with the invention, the vaccine compositions may be administered to a patient. The patient may be any human and non-human animal susceptible to infection with the selected organism. The subject vaccines will find particular use with vertebrates such as man, and with domestic animals. Domestic animals include domestic fowl, bovine, porcine, ovine, equine, caprine, Leporidate (such as rabbits), or other animal which may be held in captivity.

Administration can be oral, parenteral, intranasal, intramuscular, intravascular, or any one or more of a variety of well-known administration routes, but preferably is oral. In farm animals, for example, the vaccine may be administered orally by incorporation of the vaccine in feed or liquid (such as water). The dosage administered may be dependent upon the age, health and weight of the patient, the type of patient, and the existence of concurrent treatment, if any.

The vaccines can be employed in dosage forms such as capsules, liquid solutions, suspensions, or elixirs, for oral administration, or sterile liquid for formulations such as solutions or suspensions for parenteral, intranasal intramuscular, or intravascular use.

The vaccines may be maintained, for example, frozen, at 4° C., or at room temperature, or lyophilized.

The invention is further illustrated by the following examples. The examples provided specifically demonstrate the capabilities of Listeria spp. vaccines of the present invention. The examples are meant to be illustrative only and are not intended to limit the present invention to the specific embodiments.

The preparation of the attenuated Listeria spp. strains of the invention and the use of those strains as vaccines are also described in detail in the examples below.

EXAMPLES

Example 1 Isolation Of *Listeria Monocytogenes* Transposon-Mediated Mutants Useful In The Invention The capacity of L. monocytogenes to enter the mammalian cell cytoplasm, grow, and spread to adjacent cells are probably all essential steps for the full expression of pathogenicity and certainly require a number of structural and regulatory components. Only one stage is thoroughly defined at the molecular level, that being entry of the bacteria into the host cytoplasm which has been directly correlated with the expression of Listeriolysin O. Based on the current understanding of the cell biology of intracellular growth, there are at least eight additional steps in the process. Using the methods discussed below, mutants defective for many of these steps have been isolated. All of the mutants described herein are of reduced virulence for mice indicating that the present in vitro system of intracellular growth and cell-to-cell spread reflects the in vivo situation. The selection methods disclosed herein are useful for the generation of novel mutants which may serve as vaccines. One method of creating mutants is through transposon-mediated mutagenesis.

Transposon-mediated insertional mutagenesis was recently demonstrated in L. monocytogenes by the introduction of the conjugative transposons Tn1545 (Gaillard et al., 1986, *Infect. Immun.* 52:50) and Tn916 (Kathariou et al., *J. Bacteriol.* 169:1291). Tn1545 was delivered into L. monocytogenes at a frequency of approximately $10^{-8}$ through conjugation with strains of L. monocytogenes harboring this transposon. Tn916 was introduced trough Tn916-containing strains of *Enterococcus faecalis* at a frequency of $10^{-6}$. These relatively low frequencies of transposition make it inconvenient to carry out large-scale mutagenesis, however, and the randomness of insertion of conjugative transposons is limited by the requirement for sequence homology between both ends of the elements and sequences surrounding the sites of integration. Cossart et al. have introduced the Tn3-like transposon Tn917 into L. monocytogenes carried on the vector pTV1 and demonstrated its utility for insertional mutagenesis. (Cossart et al., *Infect. Immun.* 57: 3629–3636). This transposon exhibits a high degree of insertional randomness in *Bacillus subtilis* as well as many other gram-positive bacteria and generates extremely stable insertional mutations. Extensive information exists concerning the physical and genetic organization of Tn917.

One target for mutation is the ability to assemble actin filaments. The mobilization of actin filaments is an essential feature of the intracellular movement and cell-to-cell spread of L. monocytogenes. Intracytoplasmic L. monocytogenes grown in the presence of cytochalasin D have little or no actin on the bacterial surface, yet in permeabilized cells, the bacteria will nucleate the assembly of actin filaments from exogenously added G-actin. Thus, the bacteria apparently possess a surface or secreted actin nucleator or a product which binds a host actin nucleator. Two classes of mutants, in addition to the hly mutants, failed to associate with F-actin, and accordingly were defective for cell-to-cell spread. However, the insertions have probably occurred in regulatory genes, since these mutants are partially defective for hemolysin production as well. These mutants are the first isolated in L. monocytogenes which fail to associate with F-actin in the cell cytoplasm, although it appears that the transposon insertion is not in a gene(s) encoding the putative actin nucleator.

Additionally, transposon and deletion mutants in ActA, an L. monocytogenes product necessary for inducing actin polymerization, are attenuated mutants that may be used in the present invention.

One class of mutants represented by DP-L867 showed a rough colonial morphology and grew as filaments. This strain appears identical to other rough isolates of L. monocytogenes hich arise spontaneously at a relatively high frequency. Like other rough mutants, this mutant was defective for the secretion of a 60-kDa polypeptide and for invasion. Rough mutants were isolated on murine fibroblasts despite having a plaque forming efficiency ten times less than normal. Once internalized, however, this mutant grew quite well in both J774 cells and Henle 407 cells.

Two classes of mutants isolated in this study showed abortive intracellular growth in which growth was initially normal, but after 4–5 generations growth ceased. Although both classes of mutants were identical inside cells, one class (DP-L758) also showed abortive extracellular growth. This mutant showed a generalized defect in secretion of a number of polypeptides. The other class of mutant (DP-L793) is absolutely normal extracellularly but behaves like DP-L758 inside cells.

Some of the mutants isolated have pleiotropic affects and may be regulatory in nature. These results, however, are consistent with other bacterial systems in which there is coordinate regulation of multiple virulence determinants. Thus, mutants have been isolated which secrete reduced hemolytic and phospholipase activities (DP-L1034), reduced hemolysin and actin nucleation (DP-L1049), and most probably numerous as yet uncharacterized gene-products.

L. monocytogenes 10403S was the parental strain used to generate mutants. All of the mutants derived from this strain are listed in Table 1 below.

TABLE 1

Bacterial Strains and Relevant Characteristics

| Strain Number | Class | Transposon | Hly | Actin | Egg Yolk Opacity |
|---|---|---|---|---|---|
| 10403S | — | none | 80 U | + | + |
| DP-L758 | 1 | Tn916 | 40 U | + | + |
| DP-L793 | 2 | Tn916 | 80 U | + | + |
| DP-L867 | 3 | TN916 | 80 U | + | + |
| DP-L967 | — | Tn917-LTV3 | 80 U | + | + |
| DP-L973 | 4 | Tn917-LTV3 | 5 U | − | +/− |
| DP-L995 | 5 | Tn917-LTV3 | 40 U | +/− | − |
| DP-L1034 | 6 | Tn917-LTV3 | <5 U | − | − |
| DP-L1044 | 7 | Tn917-LTV3 | 0 U | − | + |
| DP-L1049 | 8 | Tn917-LTV3 | 20 U | − | + |
| DP-L1054 | 9 | Tn917-LTV3 | 80 U | +/− | − |
| DP-L1107 | 10 | Tn917-LTV3 | 80 U | + | + |
| DP-L1154 | — | Tn917-LTV3 | 80 U | + | + |

| Cell to Cell Spread | Additional Comments | Growth Rate in | | Site of Insertion |
|---|---|---|---|---|
| | | J774 | Henle | |
| 8.70 +/− 3.13 | Parental | 51 | 67 | none |
| 2.10 +/− 0.57 | abortive | 80 | 194 | unknown |
| 3.80 +/− 1.40 | abortive | 79 | 88 | unknown |
| 6.50 +/− 2.72 | rough | 69 | 69 | unknown |
| 8.47 +/− 3.36 | control | 60 | 59 | unknown |
| 2.00 +/− 0.94 | none | 51 | 65 | base 152 |
| 2.30 +/− 1.77 | none | 54 | 86 | base 1194 |
| 1.00 +/− 0.00 | none | none | none | unknown |
| 1.00 +/− 0.00 | none | none | 244 | base 2733 |
| 1.00 +/− 0.00 | none | 64 | 79 | unknown |
| 1.30 +/− 0.48 | none | 54 | 74 | base 841 |
| 4.80 +/− 1.87 | mixed | 59 | 74 | unknown |
| 7.70 +/− 3.30 | control | 49 | 80 | unknown |

Taking advantage of the fact that Tn917 can function in L. monocytogenes, two modified forms of the transposon, Tn917-LTV1 and Tn917-LTV3 were constructed. These derivatives are designed to include the following features. First, they are carried by highly temperature sensitive derivatives of vector pE194Ts which simplifies the recovery of chromosomal insertions.

Second, they contain a promoterless copy of the *Escherichia coli* lacZ gene oriented such that insertions into chromosomal genes can generate transcriptional lacZ fusions.

The lacZ gene encodes β-galactosidase, which was used as a foreign antigen in Example 3 below to demonstrate the efficacy of a model vaccine.

Third, they contain, immediately downstream from the lacZ coding sequence, an E. coli cloning vector that includes a gene selectable in E. coli, a gene selectable in B. subtilis, ColE1 replication functions, an M13 origin of replication, and a cluster of polylinker cloning sites. The polylinker sites facilitate the recovery in E. coli of chromosomal DNA adjacent to sites of insertion, particularly DNA on the promoter-proximal side of transposon-mediated lacz fusions.

An extremely important but unanticipated advantage of these transposon derivatives is the fact that they exhibit a much higher frequency of transposition than previously described versions of Tn917 e.g. as much as 100-fold greater in B. subtilis. This simplifies obtaining libraries of transposon-mediated lac fusions in a wide range of bacteria.

To determine the randomness of Tn917 insertions in L. monocytogenes and to evaluate the utility of the modified derivatives of the transposon, several independent insertion libraries were obtained with Tn917-LTV3 and screened for various kinds of insertional mutations.

Further details of the procedures used to generate and test these mutants are provided below.

Identification and Isolation of Mutants

Two fundamentally distinct transposable elements, Tn916 and a variant of Tn917-Lac, Tn917 -LTV3, were used to construct libraries of L. monocytogenes insertion mutants. These insertion libraries were screened for mutants which formed small or abnormal plaques in mouse L2 fibroblast monolayers after three days in culture. L2 cells were used because of all the cells tested, they produced the most homogeneous and distinct plaques. However, it should be noted that the actual uptake of L. monocytogenes by L2 cells is relatively inefficient.

Putative small plaque mutants which appeared after 3 days were purified by isolating the bacteria from the plaque and repeating the plaquing procedure until a homogeneous plaque morphology was obtained (usually three cycles of plaque purification). Seventy small-plaque mutants were isolated from approximately 100,000 plaques screened derived from 19 libraries. Although this procedure facilitated screening large numbers of plaques, it is likely that some classes of mutants were missed, such as those which failed to plaque. Nevertheless, a minimum of ten different classes of mutants were isolated based on characterization which will be described below.

All of the classes formed plaques that were smaller than wildtype ranging from those being barely visible to approximately one half the size of the parental strain. One class, represented by strain DP-L1107 always showed a mixture of small and medium sized plaques and isolation and purification of bacteria from either plaque type resulted in this mixed plaque phenotype. All of the other mutants presented with a homogenous plaque morphology.

Prototype strains representing these ten classes were subjected to further study and are listed in Table 1. Some of these mutant classes were isolated repeatedly and were clearly the result of independent insertion events, while other classes were only isolated from a single library and may represent siblings. It is also noteworthy that there was little overlap in the mutants that were isolated using the two different transposable elements indicating that neither element inserts randomly and that each has different target specificity.

Mapping of Mutants

Sequence data exists for several regions of the L. monocytogenes genome. One of these is a region of approximately 10 kb which contains the promoter and structural gene for Listeriolysin O (hly), plcA and mpl. Transposon insertion sites in all of the 70 mutants were mapped by Southern blotting for their presence in the hly region and those mutants with insertions in this region were mapped in more detail. Four of the ten classes of mutants mapped to the hly region including multiple insertions in the structural gene for hly, plcA, and prfA. The precise sites of insertion in representative mutants was determined by DNA sequence analysis. The transposon insertions in the prototype strains representing the remaining six classes of mutants all mapped to unique EcoRI fragments of unknown location indicating that these six classes are separate insertions.

Extracellular Growth of Mutants

All of the mutants grew on minimal medium indicating that auxotrophs had not been isolated. In addition, eight of the ten classes of mutants showed extracellular growth rates and colonial size and morphology identical to that of wild-type. The exceptions included mutant DP-L758 which formed small colonies on all solid medium and grew to half the density of wildtype in liquid medium and mutant DP-L867 which formed rough colonies. The latter mutant appeared to be identical to rough variants which arise spontaneously in L. monocytogenes. Like other rough isolates, this strain formed filaments of non-septating rods in liquid culture. In addition, SDS-PAGE analysis of secreted proteins indicated that a single polypeptide of 60-kDa was secreted in greatly reduced amounts. Spontaneous smooth variants could be isolated, which were tetracycline sensitive, indicating that the Tn916 element had excised and suggesting that the transposon insertion caused the rough phenotype.

Hemolytic Activity of the Mutants

Transposon insertions which result in reduced or no hemolytic activity abolish the growth of L. monocytogenes in tissue culture cells of murine origin. Hence, one might have predicted that insertions in the structural gene for hly would not grow and not form a plaque. Nevertheless, mutants with insertions in the structural gene for hly were isolated. These mutants formed very tiny plaques which may reflect delayed entry into the host cell cytoplasm or possibly growth within a vacuole.

Three other classes of mutants also had reduced levels of hemolytic activity but mapped outside the hly gene. One of these mutants, represented by DP-L973, secreted only 5 units/ml of hemolytic activity and mapped to a region just 5' of prfA, while two other classes mapped to unknown regions of the chromosome. These data suggest that other genes are necessary for the expression of hemolytic activity.

Egg Yolk Opacity Activity (Phospholipase Activity) of the Mutants

L. monocytogenes produces a zone of opacity surrounding colonies grown on egg yolk which has been shown to reflect the activity of a phospholipase C. Three classes of mutants failed to produce a zone of opacity on egg yolk agar suggesting that these mutants are defective in the expression of this activity. Most interestingly, insertions in plcA lack this activity suggesting that plcA may encode the phospholipase activity or alternatively regulate the expression of the activity. Another class of mutants represented by DP-L1034 lacked the egg yolk opacity activity and were also greatly reduced in hemolytic activity. This insertion apparently affects a gene-product involved in the production of both hemolysin and phospholipase.

Growth of Mutants in J774 Cells and Henle Cells

Hemolysin has been found to be necessary for the growth of L. monocytogenes in murine macrophages and fibroblasts, but not in human epithelial cells or fibroblasts.

All of the mutants were assayed for growth in the mouse macrophage-like cell line J774 and the human epithelial cell line Henle 407. In J774 cells, the mutants fell into four classes: 1) The majority of the mutants grew like wildtype with intracellular doubling times of approximately 1 hour; 2) Mutants with less than 10% of wildtype hemolytic activity which did not grow intracellularly; 3) Mutant DP-L973, which maps to a region 5' of prfA and secretes only 5 units/ml of hemolytic activity, but grew normally in the J774 cells; 4) Two classes of mutants initially grew like wildtype but after four to five doublings growth almost ceased. These mutants are referred to as showing abortive intracellular growth. One class of these represented by DP-L793 grew identically to wildtype extracellularly, while the other class represented by DP-L758 showed abortive growth extracellularly as well.

The growth of the mutants in Henle 407 cells was similar to that in J774 cells except, mutations in hly did not abolish intracellular growth. However, mutant DP-L1034 which is defective for expression of both hemolysin and phospholipase failed to show any growth until 8 hours in culture in the Henle 407 cells. This may reflect a very low level of escape into the host cytoplasm. Since hemolytic activity is not required for growth of L. monocytogenes in Henle cells, these data suggest that the phospholipase can substitute for the hemolysin in Henle cell lines but in the absence of both hemolysin and phospholipase there is almost no intracellular growth.

Cell-to-Cell Spread of the Mutants

With the exception of the hemolysin mutants and the abortive intracellular growth mutants, the other mutants grew quite well in both the J774 cells and Henle 407 cells, yet formed small plaques. To begin characterization of the cell-biological defect in these mutants, they were observed by light microscopy in stained monolayers of infected Henle cells, J774 cells and primary cultures of bone marrow macrophages. In order to quantitate the cell-to-cell spread, bone marrow derived macrophages were used because they are best suited for visual inspection. Also, since they are primary cells, the analysis may have the most in vivo relevance. This analysis revealed that most of the mutants were indeed defective for cell-to-cell spread. The most striking example was DP-L1049 which seemed absolutely defective for intracellular spread. This mutant was unable to move within a cell or to adjacent cells. DP-L1054 and DP-L995 which map to ORF U and lack phospholipase activity were also quite defective for cell-to-cell spread although some spreading was evident. These mutants seemed capable of limited movement to the periphery of an infected cell, but were defective in the spread to adjacent cells. occasionally, bacteria could be seen in pseudopods, and some bacteria could be detected in neighboring cells. The other hly mutants showed extensive cell-to-cell spread although not to the same extent as the parental strain.

Association with F-actin

Intracytoplasmic L. monocytogenes utilize host actin filaments to mediate their spread within a cell and from cell-to-cell. Although electron microscopy is the only method which allows visualization of individual actin filaments, actin filaments associating with the bacteria can also be indirectly visualized by fluorescent microscopy using NBD-phallacidin, a reagent which binds to F-actin and not to G-actin. Thus, J774 macrophages infected with each of the mutants were stained with NBD phallacidin. Hemolysin minus mutants failed to stain with NBD phallacidin as expected due to their vacuolar compartmentalization. All of the other mutants were positive for actin polymerization with four exceptions.

The most striking example was seen for mutants DP-L1049 and DP-L973. In no cases was any evidence of NBD phallacidin staining surrounding the intracytoplasmic bacteria found. This is consistent with the absolute inability of this strain to spread cell-to-cell. However, since these mutants are as defective for hemolysin expression, the transposon insertion has likely occurred in genes which may regulate both actin polymerization as well as hemolysin expression.

Mutants DP-L1054 and DP-L995 for the most part did not stain with NBD phallacidin although an occasional bacterium could be found which stained positively. These latter mutants are affected in actin polymerization, but not to the extent of DP-L1049.

Isolation of Transposon Insertions

A single colony of L. monocytogenes DP-L910 which harbors pLTV3 was used to inoculate 2 ml of brain heart infusion containing erythromycin, lincomycin, and tetracycline, and the culture was grown overnight at 30° C. to stationary phase. The overnight culture was inoculated 1/800 into brain heart infusion containing erythromycin and lincomycin, and the bacteria containing chromosomal transposon insertions were selected for by growth with aeration at 41° C. until stationary phase. This treatment resulted in a population of cells of which 90% were $Em^r$, $Lm^r$ and $Tc^s$, indicating loss of pLTV3 with retention of transposon insertions into the chromosome. Aliquots of the culture were directly frozen in LB broth at −70° C. until later use. The frozen aliquots from a single culture will be referred to as transposon insertion libraries of L. monocytogenes.

Characterization of Insertional Mutants

A total of 1,000 colonies of L. monocytogenes from each of 10 separate transposon insertion libraries were patched onto minimal medium to screen for 18 common auxotrophic types. Mutant strains unable to grow on the minimal media were subsequently analyzed to determine their specific auxotrophic requirements, as described by Davis, R. W., D. Botstein and J. R. Roth, 1980, "Advanced bacterial genetics," p. 20, Cold Spring Harbor Laboratory, Cold Spring Harbor, N.Y. Nonhemolytic transposon insertion mutants of L. monocytogenes were isolated by plating insertion libraries directly onto blood agar and screening for colonies lacking a zone of hemolysis.

Insertional auxotrophic mutations in at least eight distinct loci were obtained indicating that "hot spots" may exist in the L. monocytogenes chromosome where Tn917 insertions are more frequent but the overall degree of randomness is of a high order. Several insertions were also obtained within the hly gene, which encodes a hemolysin protein whose activity is a critical virulence determinant of the organism. A physical analysis of these hly::Tn917-LTV3 insertions revealed them to be distributed throughout the hly coding sequence and in both orientations with respect to the transcriptional polarity of the gene. Insertions in the appropriate orientation expressed β-galactosidase at high levels. Two of the insertions were used to rescue, into E. coli, chromosomal DNA flanking the insertion junctions.

To facilitate the study of bacterial determinants of L. monocytogenes pathogenicity, transposition-proficient derivatives of Tn917-lac containing ColE1 replication functions were constructed. By using one of these derivatives (Tn917-LTV3), it was shown that Tn917 can insert into the L. monocytogenes chromosome with a relatively high degree of randomness, generating lacZ transcriptional fusions when insertions occur within genes in the appropriate orientation. The presence of ColE1 replication functions and polylinker cloning sites allowed the convenient and rapid cloning of flanking DNA. Unexpectedly, both derivatives, Tn917-LTV1 and Tn917-LTV3, exhibited enhanced transposition frequencies in B. subtilis. Although the reason for the increased transposition frequencies was not determined, it is possible that the level of expression of the Tn917 transposase is increased in these constructs due to transcriptional readthrough from within the inserted ColE1 replicons. In the case Tn917-LVT1, the lac promoter adjacent to the polylinker cluster in pBG5 is positioned appropriately to direct transcription toward the Tn917 transposase gene. This promoter is deleted in Tn917-LTV3 but is replaced by the promoter for the Tn5 $Sm^r$ gene. The increased frequencies of transposition of pLTV1 and pLTV3 greatly facilitates their use for insertional mutagenesis in B. subtilis, and potentially in other gram-positive bacteria as well, by reducing the culture volumes necessary to produce transposon insertion libraries.

Transposons Tn917-LTV1 and Tn917-LTV3 differ only in the Gram-negative antibiotic resistance marker contained within their ColE1-derived sequences. Although it is likely that the Gram-negative bla gene present in Tn917-LTV1 would not confer resistance to ampicillin in L. monocytogenes, it was considered undesirable to introduce this gene into a pathogen for which β-lactam antibiotics are clinically important therapeutics. Thus, the bla gene was replaced with the neo and ble genes from Tn5 in the construction of Tn917-LTV3. Although Tn917-LTV3 might be the transposon of choice for other Gram-positive pathogens as well (e.g., Streptococcus spp.), Tn917-LTV1 is generally more useful for insertional mutagenesis in non-pathogenic gram-positive species since it contains additional unique restriction sites within its polylinker region.

The randomness of Tn917 insertions into chromosomal targets has been most extensively investigated in B. subtilis and B. megaterium, although the transposon has been shown to function efficiently in a broad range of bacteria, including both gram-positive and gram-negative species. Particularly in B. subtilis, it would appear that insertions in some hotspot chromosomal regions are much more frequent that in others. Even within these hotspot regions, however, insertions are distributed quite randomly, and insertions outside of hotspot regions are sufficiently abundant and random to permit very effective insertional mutagenesis. Test results indicate that the same is true for L. monocytogenes. Although the distribution of insertional auxotrophic mutations was not completely random, many different kinds were recovered. Insertions within the hly gene are significantly more frequent that would be expected on a purely random basis, suggesting that this gene may be within one of the hotspot regions of the L. monocytogenes chromosome. In addition, as in B. subtilis and other bacteria, Tn917 appears to insert singly into the L. monocytogenes chromosome.

Despite the large size of Tn917-LTV3 (15.5 kilobases), its ability to (i) insert randomly into the L. monocytogenes chromosome, (ii) form transcriptional fusions with lacZ, and (iii) allow the direct cloning of DNA adjacent to insertions should ensure its utility in generating L. monocytogenes mutants. Similarly, Tn917-LTV1, which provides even greater flexibility in the choices of restriction enzymes for cloning adjacent DNA, is useful for transposon mutagenesis.

Growth of Bacteria

Bacteria were grown on either brain heart infusion agar and broth (BHI; Difco Laboratories, Inc., Detroit, Mich.) or Luria-Bertani (LB) medium. All stock cultures were stored as suspensions of cells at −70° C. in 50% glycerol. For routine use, bacteria were kept on BHI agar at room temperature. All strains harboring Tn916 were kept on BHI agar containing tetracycline at 12.5 μg/ml. *Streptococcus faecalis* CG110 was used as a donor of Tn916. Minimal medium was used to check for auxotrophs. *Escherichia coli* strain DH5a-MCR (Bethesda Research Labs, Gaithersburg, Md.) was used as the host strain for transformation.

Tissue Culture Cells and Growth Medium

The macrophage-like cell line J774 (Ralph et al., *J. Immun.* 114: 898) and the embryonic mouse fibroblast cell line CL.7 (ATCC No. TIB 80) were grown in DME supplemented with 5% FCS. The human epithelial cell line Henle 407 (ATCC No. CCL 6) and the human fetal fibroblast cell line WS1 (ATCC No. CRL 1502) were grown in a-modified Eagle's medium supplemented with 10% FCS. All cell lines were maintained in the presence of penicillin (100 U/ml) and streptomycin (10 μg/ml). Primary cultures of bone marrow-derived macrophages were established from specific pathogen-free female CD-1, ICR mice (Charles River Laboratories, Wilmington, Mass.). Cells were grown for 7 days before use in 100-mm petri dishes (Lab-Tek; American Scientific Products, McGaw Park, Ill.) in DME supplemented with 20% FCS and 30% L-cell supernatant (source of CSE-1). $8 \times 10^6$ macrophages were routinely derived from two femurs.

Isolation of Transposon Insertion Mutants

Libraries of L. monocytogenes containing insertions of a derivative of Tn917-lac, Tn917-LTV3, were generated. Each library was shown to contain numerous insertions in many different genes although hot spots were evident. Libraries were stored at −70° C. in 50% glycerol.

Libraries of L. monocytogenes containing Tn916 were generated. The L. monocytogenes::Tn916 library was grown overnight in BHI broth at 30° C. to a density of $2 \times 10^9$ bacteria per ml. One milliliter of culture was sedimented in a microcentrifuge tube (12,000×g) for 1 minute, the supernatant fluid was discarded, and the sedimented cells were washed once with 1 ml of PBS. Monolayers of J774 cells containing approximately $8 \times 10^5$ cells were infected with $4 \times 10^6$ bacteria and, after a 30 minute incubation, the monolayers were washed three times with 37° C. PBS to remove nonadherent bacteria; this was followed by the addition of 2 ml of 37° C. medium. After an additional 30 minute incubation, gentamicin sulfate and methicillin were added to final concentrations of 0.01 and 1 mg/ml, respectively. After 4 hours, the monolayers were washed three times with PBS to remove the antibiotics and then lysed with 1 ml of sterile distilled water. The recovered bacteria were grown overnight in BHI used to infect fresh J774 cell monolayers. After the third such enrichment, a population of L. monocytogenes::Tn916 mutants resistant to intracellular methicillin killing was obtained. The recovered mutants were purified by single colony isolation on blood agar.

Plaque Formation by L. Monocytogenes in L2 Cells

In all cases L2 cells were plated so that they were confluent on the day of the infection. Bacteria were grown overnight at 30° C. in BHI broth to a density of $2 \times 10^9$ cfu/ml, washed once in PBS, and suspended in PBS to the original density. In the initial screening for small plaques, L2-cells grown in 100 mm petri dishes in 10 ml of medium (DME plus 5% FBS without antibiotics) were infected with 20 μA of the washed bacterial suspension. After 1 hour, the monolayers were washed 3× with 37° C. PBS and overlaid with 10 ml of a suspension of 1% agarose containing medium plus 10 μg/ml gentamicin sulfate. A stock of 2× medium was prewarmed at 37° C. and mixed with 56° C. 2% agarose immediately before use. As an alternative to gentamicin, ampicillin at a final concentration of 2 μg/ml was used. In this case, the monolayers were infected with 1.2

μl of the washed bacterial suspension. After three days, plaques were visualized by the addition of a 10 ml overlay of 1% agarose containing medium plus 0.2% neutral red (Sigma) (neutral red is made as a 1% stock in water and filter sterilized). Plaques (about 700/plate) were visualized after 4–8 hours as clear zones in a lawn of red cells. Any plaque that was smaller than the others was picked with a sterile toothpick and grown overnight in BHI broth.

Rescreening of plaques was performed in 6 well cluster dishes (Costar, Cambridge, Mass.). Cells were infected in 2 ml of medium with 2.5 μl of bacteria. After three days, plaques were visualized by the addition of 1 ml of the neutral red solution. After purification of a small plaque mutant to homogeneity, single colonies were purified directly from a plaque. by streaking on BHI agar and stored as suspension in 50% glycerol at −70° C.

Assay for Hemolytic Activity

Hemolysin activity was assayed essentially as described by Kingdon and Sword, *Infect. Immun.* 1970, 1, 363. Briefly, twofold serial dilutions of samples were made in PBS containing 6 mM cysteine (final pH 5.8). After a 30 minute incubation at 37° C., a 1/10 volume of a 10% solution of sheep red blood cells was added to the sample. After an additional 30 minute incubation at 37° C. the tubes were subjected to centrifugation and were scored for visible hemolysis. Hemolytic units were expressed as the reciprocal of the dilution of bacterial supernatant fluid showing 50% lysis of the red blood cells.

Assay for Egg Yolk Opacity (Phospholipase Activity)

Egg yolk plates were prepared as follows. Fresh egg yolk was diluted in half with PBS and mixed vigorously. LB agar plates were overlaid with 5 ml of soft agar (0.7% agar) containing 5% egg yolk. Individual colonies were patched in triplicate and incubated at 37° C. for 2 days. A positive reaction was seen as a slight, but definitive, zone of opacity surrounding the patch.

Intracellular Growth Assay

Monolayers of tissue culture cells were grown on 12×1 mm round cover slips (Propper Manufacturing Co. Inc., Long Island City, N.Y.) in 60-mm petri dishes containing 5 ml of the appropriate medium without antibiotics. Bacteria were grown overnight in BHI broth at 30° C. and washed once with (PBS) and used to infect the monolayers. Monolayers of J774 cells were infected with $5\times10^5$ bacteria per petri plate for 30 minutes, and Henle cells were infected with $2\times10^7$ bacteria per petri plate for 60 minutes. In both cases, this resulted in the infection of approximately one bacterium per ten cells after 1 hour. After the initial infection, monolayers were washed 3× with 37° C. PBS followed by the addition of 5 ml of prewarmed medium. After 30 minutes, gentamicin sulfate was added to a final concentration of 5 μg/ml. After 1 hour, and at each subsequent time point, the number of bacteria per cover slip was determined by depositing cover slips, in triplicate, into 5 ml of sterile distilled water in a 15 ml conical tube. After mixing vigorously for 15 seconds, dilutions were plated onto BHI agar.

Cell-to-Cell Spread

Day 6 bone marrow-derived macrophages ($2\times10^6$) were deposited onto coverslips in 60 mm petri dishes containing DME supplemented with 10% FBS and 30% L-cell supernatant (source of CSF-1) the evening before use. Monolayers were infected with each of the mutants so that approximately one in fifty cells contained a single bacterium after 30 minutes of incubation. After washing 3× with 37° C. PBS, 37° C. medium was added, and after an additional 30 minutes, gentamicin sulfate was added to a final concentration of 5 μg/ml. After 8 hours, coverslips were stained with Diff-Quik (Baxter Healthcare Corp. Edison, N.J.) and examined by light microscopy. Individual foci of infection were examined, and the number of cells containing five or more bacteria were counted.

Fluorescence Labeling of F-actin

After 4 hours of infection, J774 cells on coverslips were transferred to a solution of 3.7% formaldehyde in PBS and fixed for a minimum of 15 minutes at room temperature. Next, the coverslips were incubated in a solution containing $1.7\times10^{-7}$M NBD-phallacidin (Molecular Probes, Eugene Oreg.) and 0.4% Triton X-100 at 37° C. Intracellular bacteria were stained by indirect immunofluorescence using Listeria O rabbit antiserum (Difco Laboratories, Detroit Mich.) which was added to the NBD-phallacidin solution at a 1/320 dilution. After one wash in PBS, coverslips were incubated with a 1/40 dilution of rhodamine isothiocyanate conjugated goat F(ab')$_2$ anti-rabbit IgG (Tabo Inc., Burlingame, Calif.). Coverslips were mounted in 50% glycerol in PBS for fluorescence microscopy. Bacteria were identified as staining with RITC, while bacterial associated F-actin was identified as staining with NBD.

Mapping Sites of Tn917-LTV3 Insertions

Initially, all of the mutants were mapped by Southern blotting to determine if the transposon has inserted into the hly region of the chromosome.

Southern Blot Analysis

DNA was isolated as described by Flamm et al., *Infect. Immun.* 1984, 44, 157–161. DNA restriction enzyme digests were fractionated on 1% agarose gels in TBE buffer (89 mM Tris/89 mM boric acid/2 mM EDTA, pH 8.0). The DNA fragments were subjected to acid depurination and then transferred to nitrocellulose filters by the method of Southern. The filters were hybridized with DNA probes that had been labeled in vitro with $^{32}$P. Plasmid pAM118 (Gawron-Burke and Clewell, *J. Bacteriol* 1984, 159, 214–221) containing Tn916 was digested with EcoRI and labeled with [$\alpha^{32}$P]dCTP using an oligolabeling kit (Pharmacia). Plasmid pDP102 contained a 3.2-kilobase (kb) BamHI fragment insert containing the Listeriolysin structural gene, hly, and was isolated by screening a recombinant DNA library with an oligonucleotide hybridization probe derived from the published hly sequence. DNA probes 1 and 2, which represent internal restriction fragment of hly derived from plasmid pDP102, were gel purified using low-melting-temperature agarose and labeled with 32P as above. Hybridizations were performed at 37° C. under conditions of high stringency [50% formamide/5×SSC (1 SSC is 0.15M NaCl/0.015M sodium citrate)/0.1% SDS/1×Denhardt's solution/5.6 mM Tris, pH 7.5/100 μg of sheared and denatured calf thymus DNA per ml]. After 18 hours, the filters were washed twice in 2×SSC/0.1% SDS at 24° C.; this was followed by two washes in 0.1×SSC/0.1% SDS at 50° C. Hybridization was revealed by autoradiography with XAR-5 x-ray films (Eastman Kodak) in the presence of intensifying screens at −70° C.

The exact sites of Tn917-LTV3 insertion determined by DNA sequencing the cloned transposon-chromosomal junctions. Dideoxy sequencing of double-stranded plasmid DNA was performed as recommended by the manufacturer using a Sequenase 2.0 kit (United States Biochemical Corporation, Cleveland, Ohio). Junction sequences were obtained using an oligonucleotide sequencing primer, which was complementary to a sequence 83 bp from the lacZ-proximal end of Tn917-LTV3 (Genetic Designs, Inc., Houston, Tex.). The precise site of L. monocytogenes sequences flanking transposon insertions mapping within the hly region were identified using DNA Strider 1.0 software by searching the previously published sequence of the hly region.

The transposon insertion mutants not mapping to the hly region of the L. monocytogenes chromosome were grouped based on their phenotype and according to the size of the EcoRl fragment which resulted after insertion of the transposon.

Since neither transposon (Tn916 and Tn917-LTV3) contain an EcoRI site, a single hybridizing band was revealed for each mutant. To determine the relative sizes of these transposon-containing EcoRI fragments, Southern blotting of EcoRI digested chromosomal DNA was performed as previously described except that agarose gel electrophoresis was performed in 0.4% agarose.

Example 2 Isolation of *Listeria Monocytogenes* Deletion Mutants Useful in the Invention As described in the example below, the attenuated L. monocytogenes strains for use in vaccines of the present invention may be generated, for example, by deletion mutations rather than transposon-mediated mutations. Advantages of using deletion mutants include, for example, their greater stability over transposon-mediated mutants and the lack of associated antibiotic resistance.

Plasmid Constructions

Using the published sequence of the plcA gene (Mengaud et al., *Infect. Immun.* 1989 57, 3695–3701), PCR was used to amplify the gene from chromosomal DNA. The amplified product was then ligated into pAM401 using SalI- and XbaI-generated DNA ends to generate pDP1462.

Plasmid pDP1500, containing prfA alone, was constructed by deleting the plcA gene, bases 429 to 1349 (Mengaud et al., supra), from pDP1462 after restriction with XbaI and PstI, treatment of the DNA ends with T4 DNA polymerase to make them blunt, and intramolecular ligation.

Plasmid pDP1499, containing the plcA promoter and a portion of the 3' end of plcA, was constructed by deleting a plcA internal fragment, bases 428 to 882 (Mengaud et al., *Infect. Immun.* 1989 57, 3695–3701), from pDP1339 after restriction with PstI and NsiI and intramolecular ligation.

pDP1526 (pKSV7::ΔplcA) was constructed by a single three-part ligation of pKSV7 restricted with BAMHI and XbaI, the 468 bp XbaI and NsiI-generated fragment from pAM401::plcA containing the 5' end of plcA (bases 882 to 1351; Mengaud et al., supra) and, the 501 bp PstI- and BamHI-generated fragment from pAM401::plcA prfA containing the 3' end of plcA (bases 77 to 429; Mengaud et al., supra).

The prfA promoter, bases 1–429 (Mengaud et al., supra), was isolated by EcoRI and PstI double digestion of pDP1462 and the fragment was subsequently ligated into EcoRI-and PstI-restricted pKSV7 to generate pDP1498. Two random HindIII-generated 10403S chromosomal DNA fragments, approximately 3kb in length, were ligated into HindIII-restricted pKSV7, to generate the random integration control plasmids pDP1519 and pDP1521.

Construction of L. Monocytogenes Mutant Strains

L. monocytogenes strain DP-L1387 was isolated as a mutant with reduced lecithinase (PC-PLC) from a Tn917-LTV3 bank of SLCC 5764, constructed as previously described (Camilli et al., *J. Bacteriol.* 1990, 172, 3738–3744). The site of Tn917-LTV3 insertion was determined by sequencing one transposon-chromosomal DNA junction as previously described (Sun et al., *Infect. Immun.* 1990 58, 3770–3778). L. monocytogenes was transformed with plasmid DNA as previously described (Camilli et al., supra). Selective pressure for maintenance of pAM401, pKSV7, and their derivatives in L. monocytogenes was exerted in the presence of 10 μg of chloramphenicol per ml of media. In addition, maintenance of pKSV7 derivatives required growth at 30° C., a permissive temperature for plasmid replication in Gram-positive bacteria.

Integration of pKSV7 derivatives into the L. monocytogenes chromosome occurred by homologous recombination between L. monocytogenes DNA sequences on the plasmids and their corresponding chromosomal alleles. Integration mutants were enriched by growth for approximately 30 generations at 40° C., a non-permissive temperature for pKSV7 replication, in Brain Heart Infusion (BHI) broth containing 10 μg chloramphenicol per ml of media. Each integration strain was subsequently colony purified on BHI agar containing 10 μg chloramphenicol per ml of media and incubated at 40° C. Southern blot analyses of chromosomal DNA isolated from each integration strain confirmed the presence of the integrated plasmid.

Construction of DP-L1552 containing a ΔplcA allele on the chromosome is shown schematically in FIG. 1. Integration of the pKSV7 derivative, pDP1526, to generate a merodiploid intermediate was done as described above. Spontaneous excision of the integrated plasmid, through intramolecular homologous recombination, occurred at a low frequency. Bacteria in which the plasmid had excised from the chromosome were enriched by growth at 30° C. in BHI broth for approximately 50 generations. The nature of the selective pressure during this step was not known but may be due to a slight growth defect of strains containing integrated temperature-sensitive plasmids. Approximately 50% of excision events, i.e., those resulting from homologous recombination between sequences 3' of the deletion, resulted in allelic exchange of ΔplcA for the wild-type allele on the chromosome.

The excised plasmids were cured by growing the bacteria at 40° C. in BHI for approximately 30 generations. Bacteria cured of the plasmid retaining the ΔplcA allele on the chromosome were identified by their failure to produce a zone of turbidity surrounding colonies after growth on BHI agar plates containing a 5 ml overlay of BHI agar/2.5% egg yolk/2.5% phosphate-buffered saline (PBS) (BHI/egg yolk agar). The turbid zones resulted from PI-PLC hydrolysis of PI in the egg yolk, giving an insoluble diacylglycerol precipitate. The correct plcA deletion on the L. monocytogenes chromosome was confirmed by amplifying the deleted allele using PCR and sequencing across the deletion.

Using mutants, it was found that readthrough transcription of prfA from the plcA gene promoter is necessary for expression of genes required for cell-to-cell spread. PI-PLC is required for efficient escape of L. monocytogenes from host-cell vacuoles and for wild-type levels of growth in the livers of infected mice. It is likely that PI-PLC may act in concert with LLO within acidified vacuoles of the host cell to mediate lysis of the vacuolar membrane. Although PI-PLC is not an essential determinant of pathogenicity in the mouse model (in contrast to LLO) it nevertheless clearly plays a significant role in the growth of L. monocytogenes in some host tissues.

Thus, PI-PLC negative mutants (plcA deletion mutants) may be used according to the present invention to generate attenuated L. monocytogenes vaccines. Other mutants were made using the same method, namely, an actA deletion mutant, a plcB deletion mutant, and a double mutant lacking both plcA and plcB, all of which may also be used according to the present disclosure to generate attenuated L. monocytogenes vaccines. Given the present disclosure, one skilled in the art would be able to create other attenuated mutants in addition to those mentioned above.

Example 3 β-Galactosidase as Foreign Antigen

Brown et al. , *J. Infect. Diseases* 1987, 155, 86–92, disclose that attenuated Salmonellae may be expected to elicit both humoral and cellular responses to intracellular cloned antigens. An attenuated Salmonella strain was used as a carrier for a plasmid directing the expression of β-galactosidase in Salmonellae, which do not normally produce this protein. The resulting strain expressed β-galactosidase as an intracellular antigen.

In addition, recombinant BCG strains have been used to develop vaccines. As a model, the E. coli lacZ gene which produces β-galactosidase was introduced into BCG using a vector and subsequently tested for its ability to generate an immune response. Stover et al., Nature 1991 351, 456–460. Thus, the expression of β-galactosidase has been an accepted model for determining the ability to elicit an immune response.

Further, murine listeriosis has been extensively studied as a model for infections in which antibody plays little or no role. Immunity to L. monocytogenes requires prior administration of sublethal doses of live bacteria or, alternatively, adoptive transfer of immune CD8$^+$T-cells, although innate immune mechanisms are also crucial. Thus, murine listeriosis is an excellent system for the study of host-parasite interactions for infections which require the induction of cell-mediated immunity.

Using a model vaccine of the present invention, a cytotoxic T-cell (CTL) response to a recombinant antigen expressed by Listeria monocytogenes has been successfully induced. An antigen, β-galactosidase, was introduced into the L. monocytogenes chromosome as a Tn917-lac insertion as described in above. The strain DP-L967 was chosen because it produces relatively large amounts of the enzyme. The enzyme is not secreted by L. monocytogenes, but it is expressed by L. monocytogenes in macrophages.

BALB/c mice were immunized i.p. with either L. monocytogenes strain 10403S or DP-L967 and boosted at 1 month, and their spleens were harvested 1 week later. Cells were restimulated weekly in vitro with a β-galactosidase-expressing transfectant tumor line (C3-4) and tested for their ability to lyse β-galactosidase targets specifically. As a positive control, cells from mice that had been injected 8 days previously with syngeneic spleen cells cytoplasmically loaded with β-galactosidase were also stimulated in vitro with C3-4 cells. See Schafer et al., J. Immunol. 1992 149, 53–59.

Figure 2A:
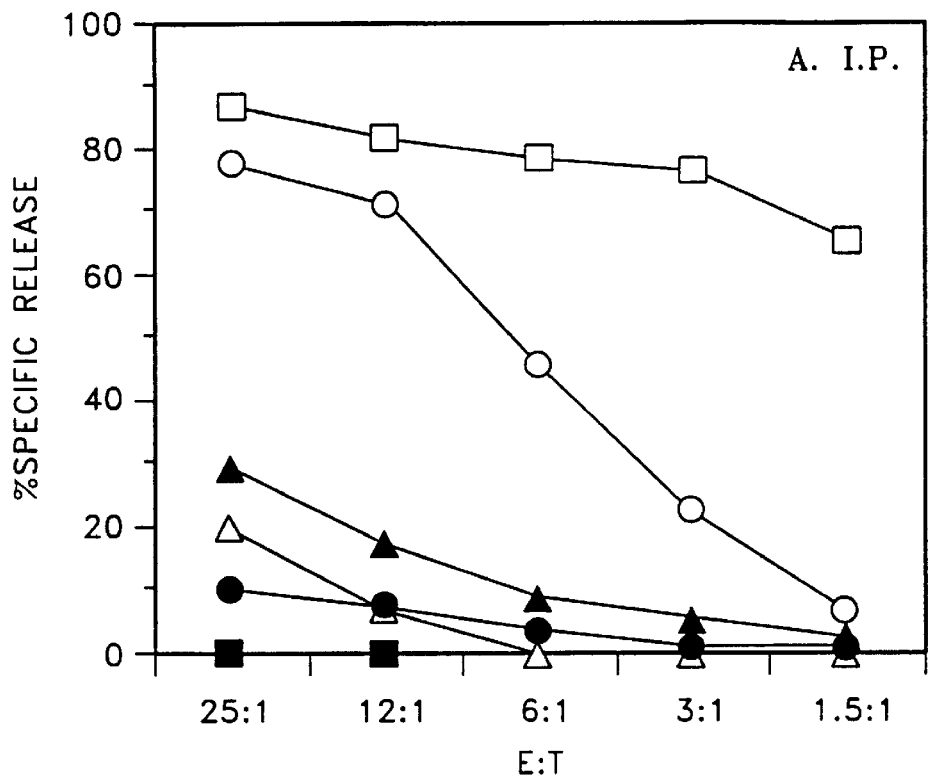
FIG. 2A is a graph representing the cytotoxic activity of spleen cells from mice immunized once i.v. with syngeneic β-galactosidase-loaded spleen cells (squares), twice i.p. with wild-type L. monocytogenes 10403S (triangles), or twice i.p. with L. monocytogenes DP-L967 (circles). DP-L967 is an L. monocytogenes strain derived from the wild-type strain, 10403S, and contains a chromosomal copy of the E. coli lac-Z gene. Cells were maintained in vitro for 3 to 5 weeks before testing for lysis of $^{51}$Cr-labeled P815 (tumor cell line P815 is a DBA/2, H-2 mastocytoma) (closed symbols) or P13.1 (tumor cell line P13.1 is a P815 transfectant producing β-galactosidase) (open symbols).

Cells from mice immunized i.p. with L. monocytogenes expressing β-galactosidase (DP-L967) showed a β-galactosidase-specific CTL response against P13.1 targets (FIG. 2A). In contrast, cells from mice immunized with wild-type L. monocytogenes (10403S) did not generate a specific CTL response but showed some low level background killing against both P815 and P13.1 targets (FIG. 2A). Cells from mice injected with β-galactosidase-loaded spleen cells show a specific CTL response to the β-galactosidase-expressing target (FIG. 2A).

Figure 2B:
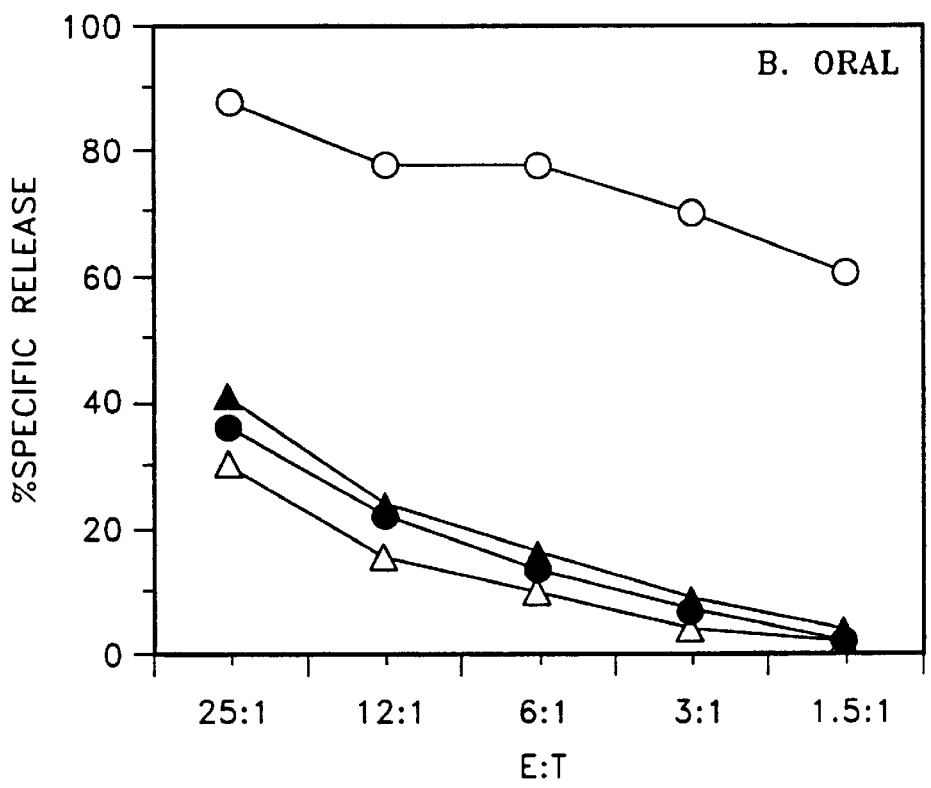
FIG. 2B is a graph showing the cytotoxic activity of spleen cells from mice immunized twice orally with wild-type L. monocytogenes 10403S (triangles) or with L. monocytogenes DP-L967 (circles). Cells were maintained in vitro for 3 weeks with C3-4 stimulator cells (tumor cell line C3-4 is a transfectant of the BALB/c hybridoma igm 662, which expresses cytoplasmic β-galactosidase) before testing for lysis of $^{51}$Cr-labeled P815 (closed symbols) or P13.1 (open symbols).
Figure 3A:
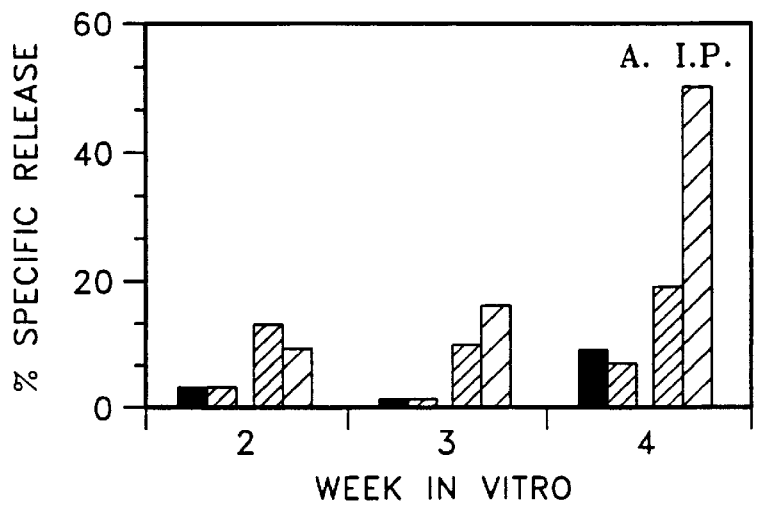
FIGS. 3A, 3B and 3C demonstrates the selection of β-galactosidase-specific CTL in vitro. Cytotoxic activity of spleen cells from mice immunized i.p.
Figure 3B:
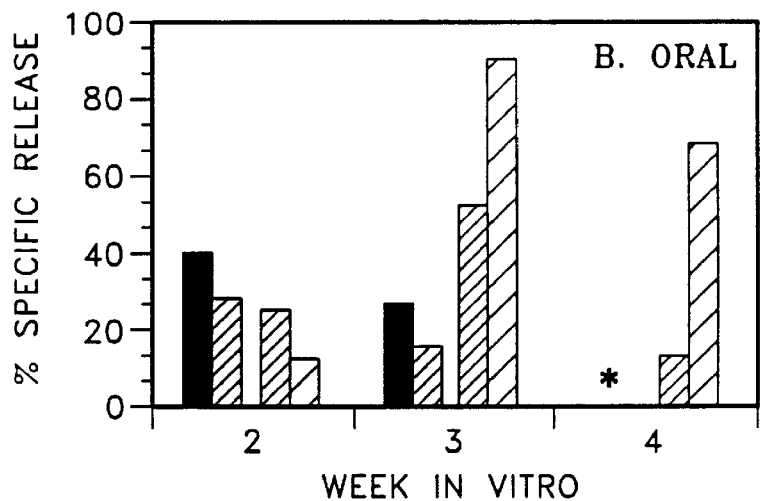

Mice were also twice inoculated orally with live L. monocytogenes strain 10403S or DP-L967 to determine whether CTL could be elicited through the natural route of infection. Spleen cells taken 1 week after the second inoculation were restimulated weekly with C3-4 cells, as described above, and tested for cytolytic activity. It was found that cells from mice given the recombinant L. monocytogenes (DP-L967), but not wild-type L. monocytogenes (10403S), specifically killed β-galactosidase targets (FIG. 2B). Similar results were seen with spleen cells taken 1 week after a single oral inoculation with DP-L967 and restimulated with C3-4 cells (FIG. 3B). These results demonstrate the efficacy of oral inoculation for the generation of specific CTL response.

Figure 3C:
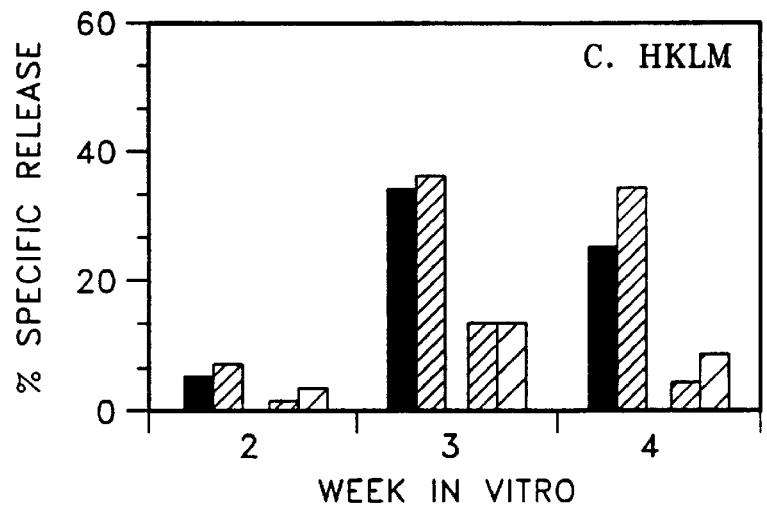

A consistent finding in these studies was that it took approximately 4 to 5 weeks of in vitro restimulation with C3-4 sells to select the β-galactosidase-specific effector population. This was true after both i.p. (FIG. 3A) and oral (FIG. 3B) inoculations. As shown in FIG. 3, after 2 to 3 weeks in vitro there was low level nonspecific killing by cells from mice immunized with either the recombinant L. monocytogenes (DP-L967) or the wild-type L. monocytogenes (10403S). After 4 weeks, cells from mice given the wild-type L. monocytogenes continued to show this nonspecific lysis, but these cells decreased in number and died. Cells from mice given the recombinant L. monocytogenes, however, continued to grow and by 4 to 6 weeks in vitro, had strong β-galactosidase specific cytolytic activity. Thus, cells from mice injected with the wild-type L. monocytogenes, or cells from naive mice, do not develop β-galactosidase-specific effectors and do not survive in vitro. Further, heat-killed L. monocytogenes does not provide an effective cytotoxic T-cell response, as seen in FIG. 3C.

These findings were very reproducible, since, in seven different experiments in which mice were immunized parenterally (five times i.p. or twice i.v.) with either wild-type (10403S) or β-galactosidase-expressing L. monocytogenes (DP-L967), spleen cells from the mice immunized with 10403S failed to survive in culture on stimulation with C3-4 cells, whereas spleen cells from mice immunized with DP-L967 consistently survive in culture to produce β-galactosidase-specific CTL lines that displayed the specificity and cytotoxicity shown in FIG. 2. Similar results were obtained in three separate experiments in which mice were immunized orally with either 10403S or DP-L967. In addition, normal spleen cells from naive mice could not be primed with C3-4 cells in vitro. These results suggest that the generation of β-galactosidase-specific CTL is not due to in vitro priming with C3-4 cells but depends on in vivo immunization with the recombinant L. monocytogenes expressing β-galactosidase. This example thus demonstrates that a cytotoxic T-cell response can be achieved to a foreign recombinant antigen expressed by live Listeria monocytogenes. Additionally, the foreign antigen need not be secreted by L. monocytogenes to generate a T-cell response.

Example 4 Influenza

Vaccines of the invention were developed and tested using an embodiment capable of creating murine immunity to influenza virus. The advantages to the influenza system include, for example, 1) a well-characterized immune response in the mouse; 2) known antigens recognized by both the humoral and cellular immune response; 3) known peptides recognized by T-cells within different mouse haplotypes; 4) the importance of cytotoxic T-cells in protection against the virus; and 5) similarities between influenza and HIV in evading the immune response. For example, influenza kills mice and therefore can be used in protection studies to verify the efficacy of the vaccine in protecting against a lethal challenge with the virus. Further, both influenza and HIV undergo antigenic variation.

This embodiment of the present invention demonstrates the ability of L. monocytogenes to secrete a foreign antigen in vivo, and the extent of the murine response to the foreign antigen. Expression and response to the Influenza Nuclear Protein (NP), the antigen tested, is described below. The bulk (80%) of the CTL response to Influenza in a Balb/c mouse is to NP. The precise peptide sequence that is recognized is derived from amino acids 147–158.

It is believed that cytotoxic T-cells (CTLs) recognize antigen derived from the cellular cytoplasmic compartment.

Figure 7:
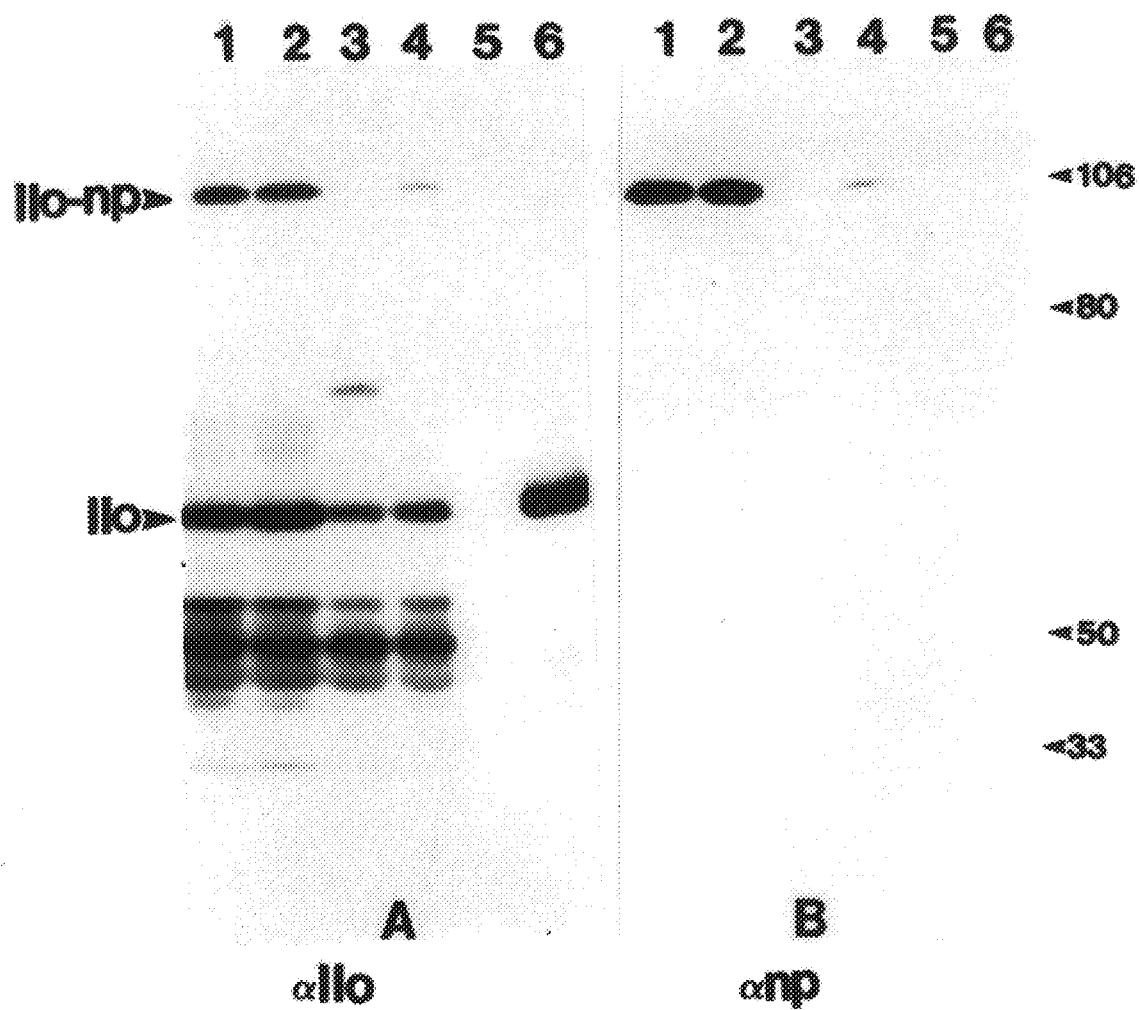
FIG. 7 represents a Western immunoblot of Listeria monocytogenes secreted proteins, as described in Example 3. The antiserum used in panel A was a rabbit polyclonal sera specific for Listeriolysin O. Binding of the antiserum to the filter was detected with $^{125}$I-labeled Protein A. The antiserum used in panel B was a mouse monoclonal antibody specific to influenza nucleoprotein (NP). Binding of the monoclonal antibody to the filter was detected with $^{125}$I-labeled goat anti-mouse IgG.

Therefore, proteins secreted by L. monocytogenes directly into the cytoplasm of a host cell, upon genetically engineering L. monocytogenes according to the present invention, should be available for presentation with Class I antigens.

One embodiment of a vaccine directed against influenza provides fusion proteins of NP with Listeriolysin O (LLO). LLO is a secreted protein which is required by L. monocytogenes to lyse the host cell vacuole and thus enter the cytoplasm. Furthermore, LLO has been shown to be a major antigen recognized by cytotoxic T-cells in Balb/c mice. Palmer et al., *Nature,* 1991, 353, 852–855; Bouwer et al., *J. Exp. Med.,* 1992, 175, 1467–1471. Therefore LLO is expressed in vivo and recognized by the immune system.

According to this embodiment of the invention, a secreted fusion protein comprised of LLO and NP is subject to recognition by cytotoxic T-cells. However, based on the prior art, it was not known if such a fusion protein would be secreted. Furthermore, it was not clear from the prior art whether, even if it was secreted, if it would generate a cytotoxic T-cell response. Additionally, it was not known, based on the prior art, even if cytotoxic T-cells were generated, whether they would recognize the same peptide sequence that is recognized during normal influenza infection.

For example, there is disagreement within the scientific community as to whether the sequences flanking an antigenic sequence influence its processing and presentation to cytotoxic T-cells. At least two groups suggest that the processing and presentation of an antigen are affected by flanking sequences (Del Val et al., *Cell* 1991 66, 1145–1153 and Eisenlohr et al., *J. Exp. Med.* 1992, 175, 481–487 ), while one group maintains that presentation is independent of the position of the antigenic sequence (Hahn et al., *J. Exp. Med.* 1991 174, 733–736). Thus, it was unclear whether the sequences in a fusion protein which are other than NP sequences would prevent the proper processing and presentation of antigenic NP sequences. The present disclosure demonstrates that the fusion peptide is properly processed and presented and thus is capable of generating a cytotoxic T-cell response that is reactive with the antigenic NP sequences resulting from an influenza infection.

Specifically, the results shown in FIG. 4 indicate that the cytotoxic T-cell response is not directed to cells that do not express the NP peptide (FIG. 4B) but rather the response is antigen-specific for cells expressing the NP peptide (FIG. 4A). Further, the data demonstrates that only L. monocytogenes expressing the NP fusion protein generate the cytotoxic T-cell response.

The data presented in FIG. 5 demonstrates that the same peptide sequence recognized during a normal infection is recognized by the cytotoxic T-cells generated against a fusion protein. Further, this figure demonstrates that the cytotoxic T-cells are influenza-specific. The data represented in FIG. 6 demonstrates that the cytotoxic T-cell response generated in mice by a normal influenza infection kills cells infected with L. monocytogenes expressing NP, and not cells infected with wild-type L. monocytogenes. Thus, the cytotoxic T-cell response specific for influenza recognizes NP secreted by L. monocytogenes.

Further details of the procedures used to generate and test this vaccine are presented below.

Genetic Construction of LLO-NP

Using PCR technology and the published sequences of the hly gene and the NP gene, (Mengaud et al., *Infect. Immun.* 1988, 56, 766–772; Palese, and Kingsbury (Eds), *The Genetics of Influenza viruses*, Springer, Vienna, 1983), a fusion was constructed in *E. coli* which would encode the hly promoter and the first 416 amino acids of LLO fused in-frame to the entire coding sequence of NP which encodes 513 amino acids. The resulting gene fusion predicts a polypeptide of 105 kDa. The fusion gene was cloned into a shuttle plasmid pAM401 (Wirth and Clewell, *J. Bacteriol.* 1986, 165, 831–836), which can be transformed and maintained by L. monocytogenes. The plasmid is pDP1673 and the strain DP-L1659.

The recombinant strains were grown in vitro under conditions in which LLO is normally secreted into the extracellular medium. The supernatant fluid was precipitated with trichloroacetic acid and subject to electrophoresis in an SDS-polyacrylamide gel, transferred to nitrocellulose and reacted with either antibody specific for LLO or NP. The results (FIG. 7) clearly show that the recombinant L. monocytogenes strains secretes a 105 kDa protein that reacts with antiserum to LLO and NP. Thus this embodiment of the present invention demonstrates a recombinant strain of L. monocytogenes that secretes a fusion protein consisting of LLO and NP.

Advantages of a hemolysin fusion protein include, for example, the secretion of the foreign antigen at the same time as hemolysin, which allows L. monocytogenes to enter the cytoplasm of the host cell. Thus, the foreign antigen may be more likely to appear within the host cytoplasm at an appropriate time in the cycle of L. monocytogenes infection to generate a CTL response against the foreign antigen.

Stability of the Plasmid in vivo

The recombinant strain (0.1 $LD_{50S}$ of the wildtype strain) was injected i.v. into Balb/c mice, and after 48 hours, bacteria present in the liver and spleen were plated on agar medium. The stability of the plasmid was evaluated by their resistance to the plasmid-encoded antibiotic (chloramphenicol). The results showed that the plasmid was lost in vivo. Less than 1% of the recovered bacteria were resistant to chloramphenicol. Therefore, this construct was not adequate for the evaluation of a T-cell response to NP.

Construction of a Plasmid which is Stable in vivo

It was believed that plasmid pDP1673 was unstable in vivo due to the presence of the hly promoter or due to the expression of the fusion protein. Nevertheless, it is clear that the plasmid is selected against in vivo. Therefore, it was desirable to insert a gene into this plasmid which would be essential for L. monocytogenes growth in vivo. Therefore, the gene prfA was cloned into the plasmid, generating pDP2028. prfA encodes a positive regulatory factor required for LLO expression and virulence. Mutants lacking prfA are completely avirulent. However, prfA mutants can be fully complemented by providing a copy of prfA in trans cloned on pAM401. Therefore, pDP2028 was transformed into the prfA minus strain DP-L1075. The resulting strain has an $LD_{50}$ of approximately $2\times10^8$ compared to $2\times10^4$ for the wildtype strain. The severe decrease in virulence might be caused by the expression of the fusion protein, and/or by the presence of the hly promoter in high copy. Nevertheless, this strain maintained the plasmid in vivo.

Bacteria were recovered from animals injected with 0.1 $LD_{50S}$ after 48 hours. Greater than 80% of the recovered bacteria were resistant to chloramphenicol. Therefore, plasmid pDP2028 is stable in vivo in a prfA minus L. monocytogenes background. As expected, the same plasmid was completely unstable in vivo when harbored by wildtype L. monocytogenes (strain DP-L2027).

FIG. 7 demonstrates that the presence of the prfA gene on the plasmid increases the amount of fusion protein secreted by *Listeria monocytogenes* in prfA- strains. Specifically, FIG. 7 represents a Western immunoblot of *Listeria monocytogenes* secreted proteins. In each case, bacteria were grown in 20 ml of brain heart infusion medium to stationary phase and subject to centrifugation. The protein was precipitated from the supernatant fluid with 10% trichloroacetic acid at 4° C. for 1 hour. The precipitated protein was subject to centrifugation and the pellet suspended in final sample buffer. Approximately 8 mls equivalent of culture supernatant fluid was subject to electrophoresis in an 8%-SDS-polyacrylamide gel. The gel was transferred to nitrocellulose by electroblotting and reacted with antiserum as described in the figure legend.

Generation of a CTL Response by the Recombinant Strain

Both wildtype L. monocytogenes and strain DP-L2028 which stably expresses the LLO-NP fusion were injected i.v. in Balb/c mice using doses of 0.01, 0.001, and 0.0001 $LD_{50}s$ for the recombinant strain, and 1 $LD_{50}$ for the wildtype strain. After four days, spleens were removed and splenocytes were stimulated in vitro for 4 days with a synthetic peptide derived from amino acids 147–158 of NP. The cytolytic activity of the population was measured in a 4 hour $^{51}Cr$-release assay against P815 cells pulsed with the identical peptide.

Figure 4A:
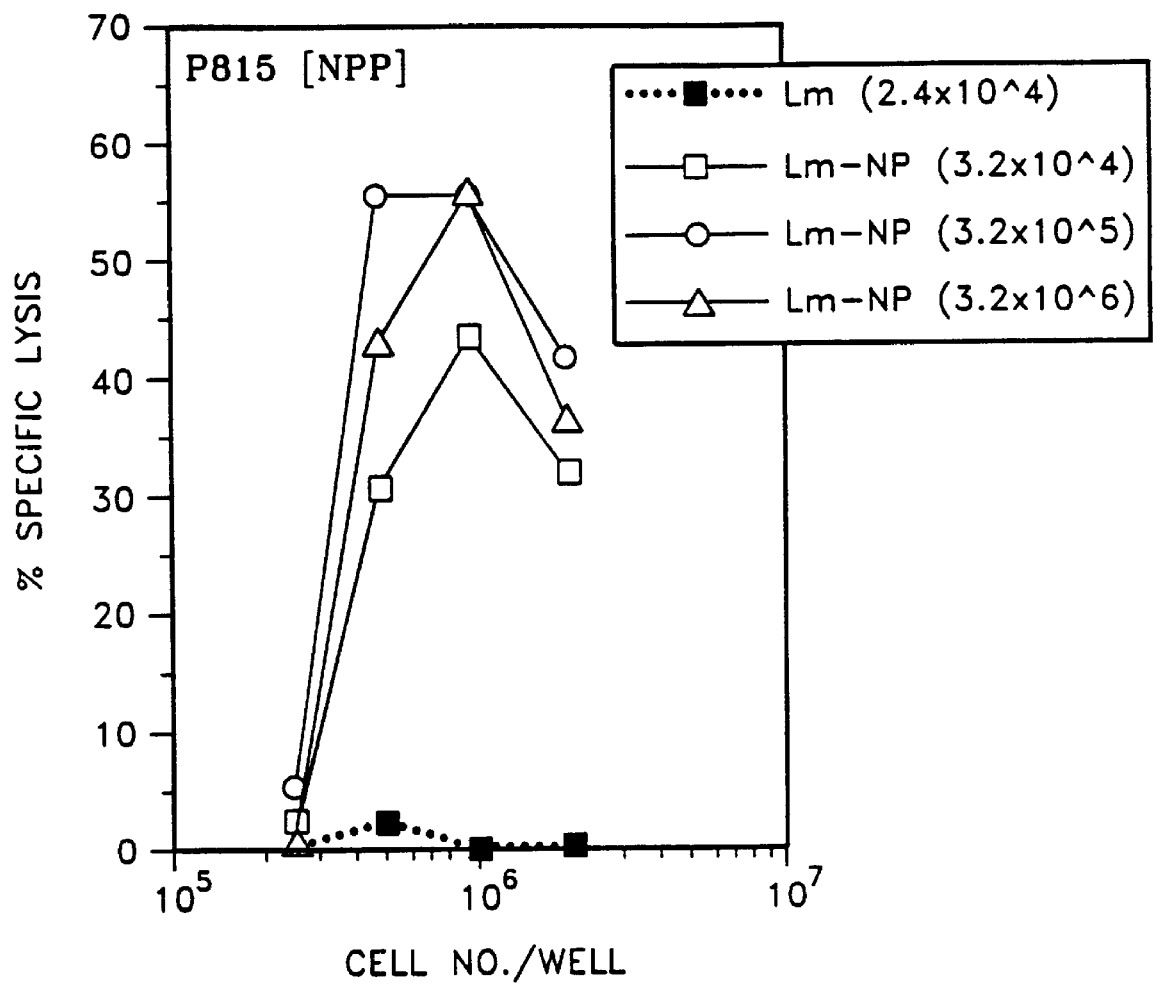
FIG. 4A depicts the generation of NP-specific CTL by in vivo immunization with Lm-NP. BALB/c (H-$2^d$) mice were immunized i.v. with L. monocytogenes strain DP-L2028 expressing influenza A virus nucleoprotein (Lm-NP). After 8 days, spleens were removed and splenocytes were stimulated in vitro for 4 days with a short synthetic peptide (NPP) with a modified sequence 147–158 (R156) derived from influenza A virus nucleoprotein with high affinity for K class I MHC molecules. See, for example, Bodmer et al., Cell 1988 52, 253. This is a more antigenic peptide than the naturally occurring peptide spanning sequences 147–158, which has an arginine at position 156. The cytolytic activity of generated effector CTL was measured in a 4 hour $^{51}$Cr-release assay against NPP-pulsed P815 (H-$2^d$) target cells, with the number of target cells being $10^4$.
Figure 4B:
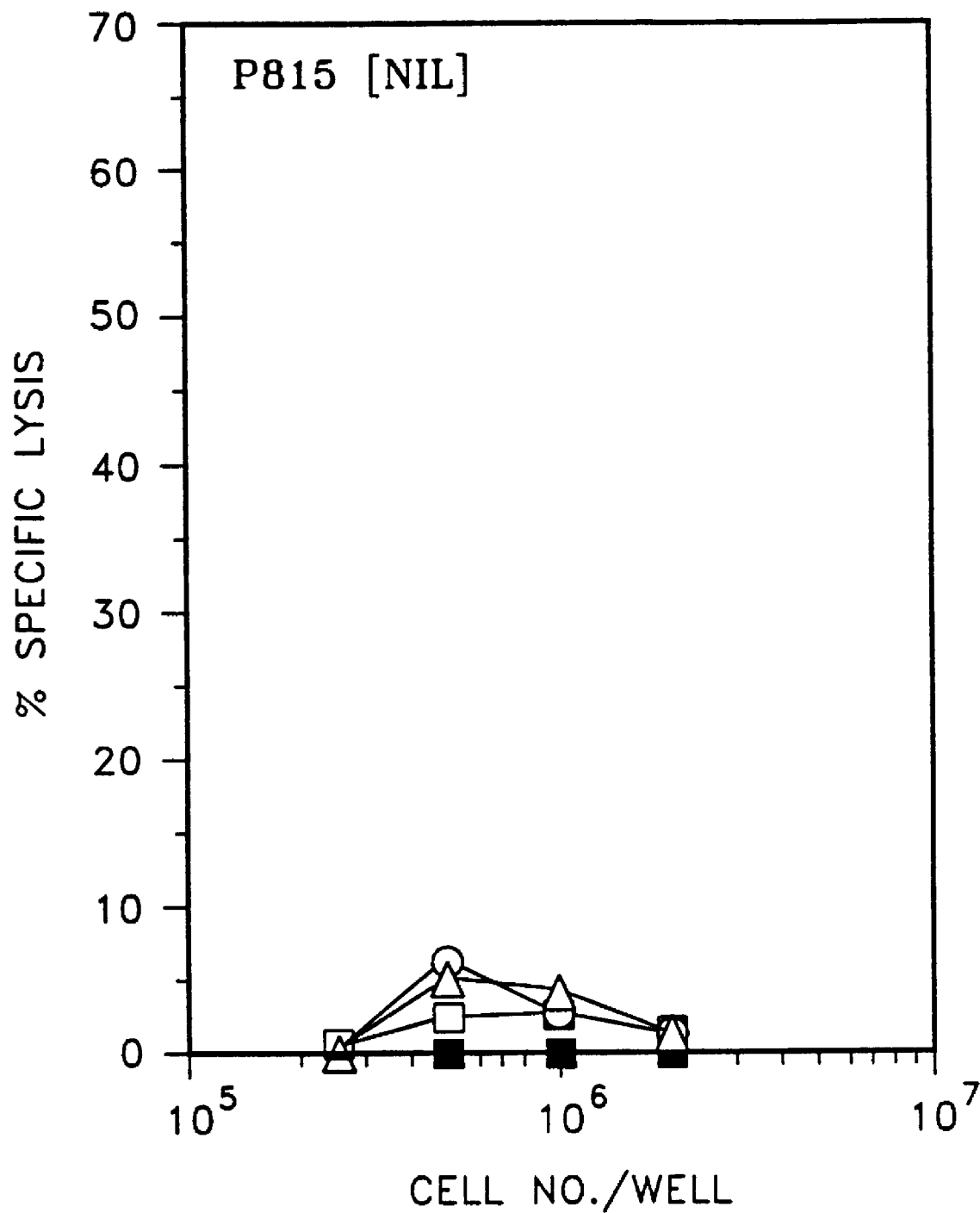
FIG. 4B illustrates a control experiment using tumor cells that do not express the NP fusion protein. Specifically, the cytolytic activity of generated effector CTL was measured in a 4 hour $^{51}$Cr-release assay against untreated P815 (H-$2^d$) target cells, with the number of target cells being $10^4$.
Figure 5:
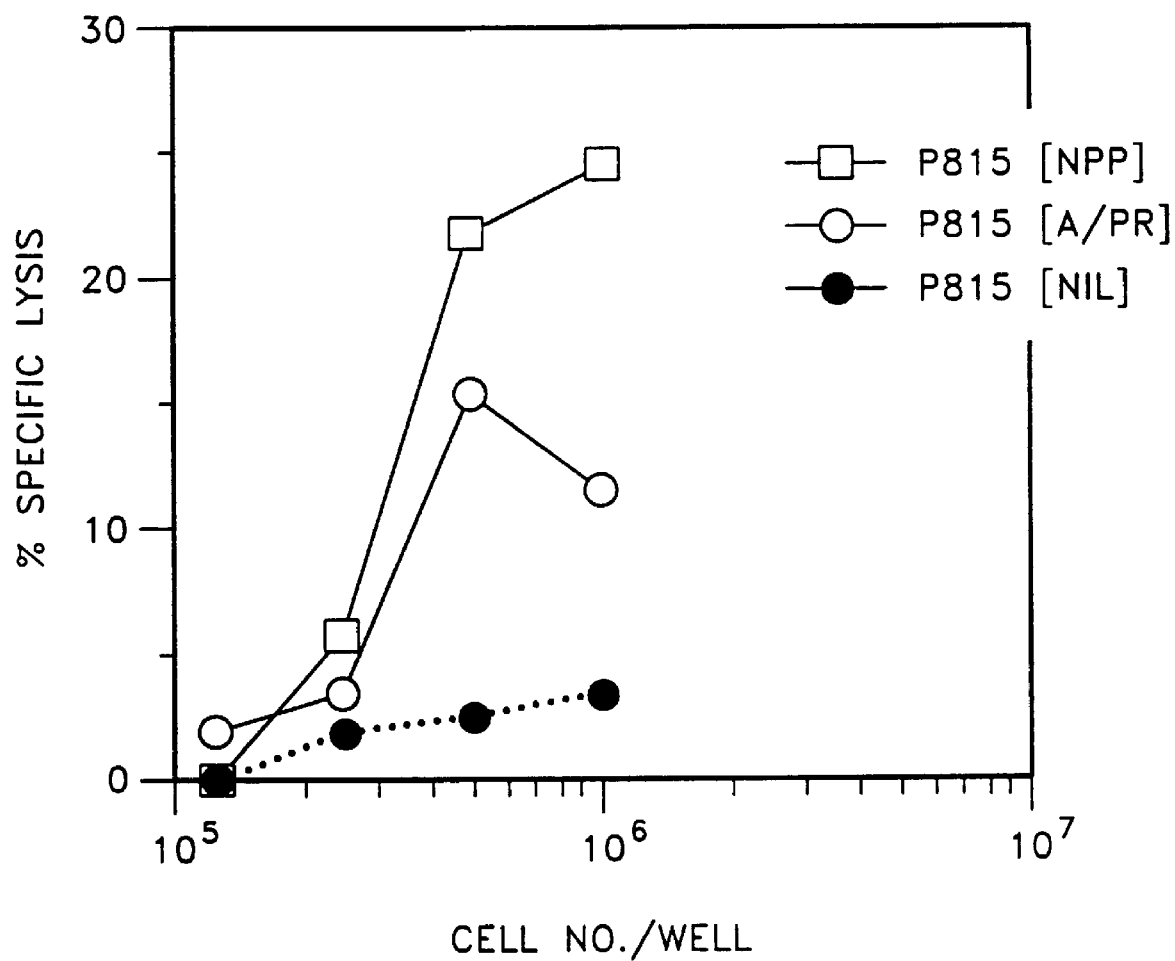
FIG. 5 shows the activity of CTL generated from NPP-stimulated splenocytes. BALB/c mice were immunized i.v. with $L_m$-NP ($1\times10^8$/mouse) and after 4 weeks, the activity of CTL generated from NPP-stimulated splenocytes was measured in a 4 hour $^{51}$Cr release assay against uninfected (P815 [NIL]), influenza A/PR-infected (P815 [A/PR]) and NPP-pulsed (815 [NPP]) P815 target cells, with the number of target cells being $2\times10^4$.
Figure 6:
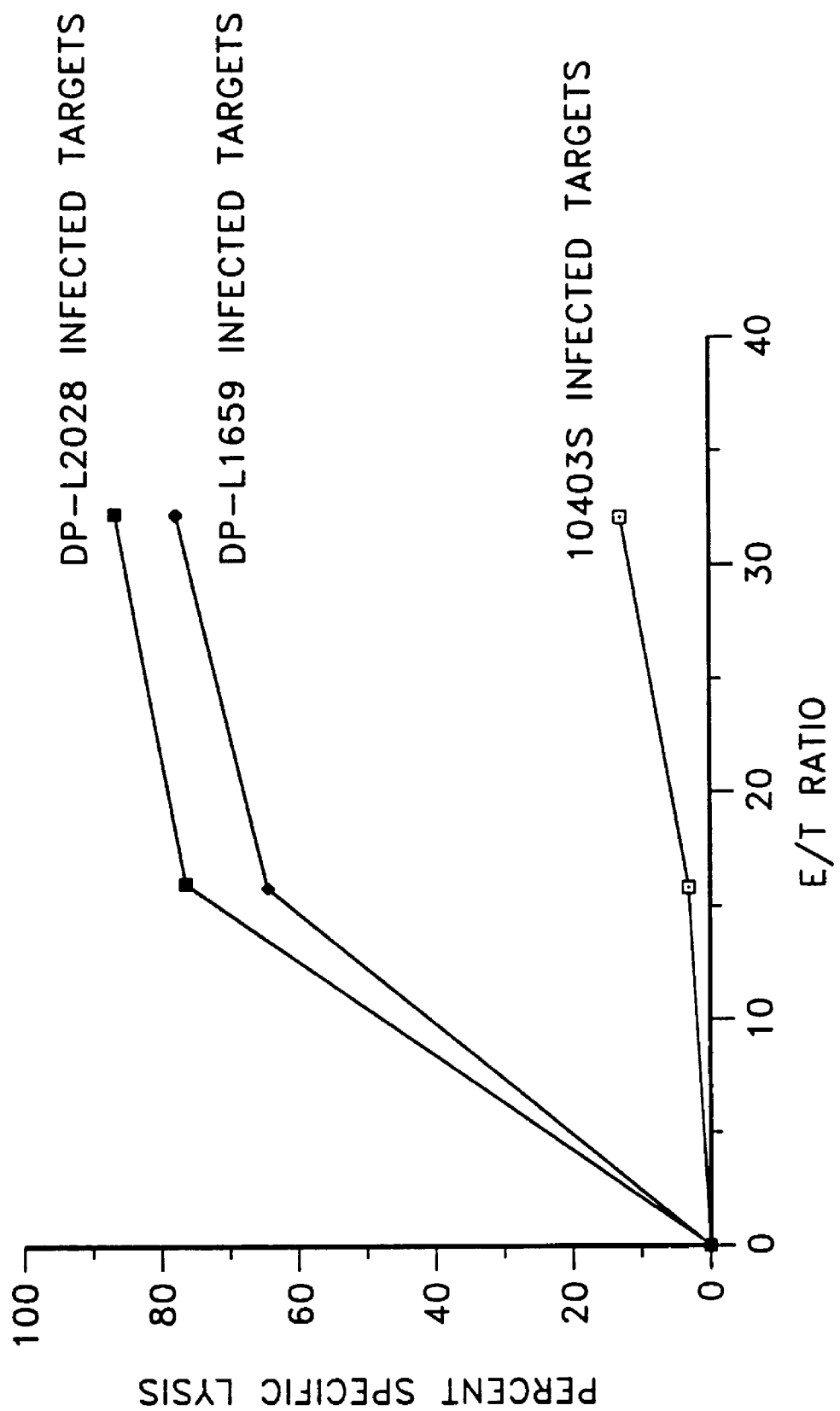
FIG. 6 illustrates specific cytotoxicity of splenocytes from mice primed with influenza virus against J774 cells infected with three different Listeria monocytogenes strains, as described in Example 3. 10403S is the parental strain. DP-L1659 represents 10403S transformed with pAM401 containing the LLO-NP fusion. DP-L2028 is DP-L1075 containing pAM401 which includes the LLO-NP fusion and the prfA gene. Splenocytes were added at the indicated effector/target ratios and allowed to interact with the infected J774 cells for 3 hours.

The results clearly showed specific lysis of the targets using splenocytes from mice infected with the all of the doses of the recombinant strain, while mice infected with wildtype L. monocytogenes showed no CTL response (FIG. 4A). None of the splenocyte populations recognized non-peptide pulsed P815 cells (FIG. 4B). Splenocytes isolated from mice four weeks after immunization were also able to recognize target cells although at a reduced amount (FIG. 5), indicating that immunity is long-lived. Further, P815 cells infected with type A influenza (A/PR8/34) were killed by the cytotoxic T-cells generated by immunization with L. monocytogenes expressing the fusion peptide (FIG. 5, P815[APR]). Therefore, this embodiment of the present invention demonstrates that L. monocytogenes expressing a secreted fusion LLO-NP polypeptide induces the production of CTLs directed against the same amino acid sequence of NP as induced by Influenza virus.

FIG. 6 illustrates specific cytotoxicity of splenocytes from mice primed with influenza virus against J774 cells infected with three different *Listeria monocytogenes* strains. 10403S is the wild-type parental strain. 1659 represents 10403S transformed with pAM401 containing the LLONP fusion. 2028 is DP-L1075 containing pAM401 containing the LLO-NP fusion and the prfA gene.

Mice were immunized with influenza A/PR/8 i.p. and after 3 weeks, the spleens were removed and the splenocytes were stimulated in vitro for 5 days with a peptide containing NP amino acids 148–157 at a concentration of $10^{-8}$.

The cytotoxicity assay was adapted from Barry et al., *Infec. Immun.* 60, 1625–1632. J774 macrophage-like cells ($3\times10^5$/well) grown on three 12 mm round glass coverslips were infected with bacteria for 30 minutes, washed, and after 30 minutes, gentamicin sulfate was added at a final concentration of 30 micrograms/ml. The gentamicin kills extracellular bacteria but does not affect intracellular bacteria. After 4 hours of intracellular growth, tetracycline was added to a final concentration of 12.5 micrograms/ml to inhibit further bacterial growth. Tetracycline is bacteriostatic for the intracellular L. monocytogenes.

After 1 hour, splenocytes were added at the indicated effector/target ratios and allowed to interact with the infected J774 cells for 3 hours. The number of bacteria/coverslip was determined by lysing the cells in distilled water and plating the bacteria on agar medium. The percent specific lysis was calculated as the difference between colony forming units without splenocytes and the number of colony forming units plus splenocytes.

Example 5 Malaria

Vaccines may be generated against malaria using the disclosure of the present invention to create an expression system in L. monocytogenes in which a malaria antigen is expressed. For example, a fusion protein between the L. monocytogenes LLO protein and the Plasmodium falciparum circumsporozite antigen may be created using PCR technology since the DNA sequences are known. The DNA encoding the fusion protein may be inserted, for example, into plasmid pAM401 which contains the L. monocytogenes prfA gene. The plasmid may then be stably maintained in L. monocytogenes, for example, by transforming the plasmid into a prfA minus mutant of L. monocytogenes. Like the other examples of the invention, it is believed that this fusion protein would be secreted and may generate a cell-mediated immune response upon administration to a vertebrate.

Example 6 HIV

Certain biological properties of HIV-1 make it a difficult target for immunization as well as treatment. The vaccines of the present invention using L. monocytogenes offer these advantages, for example, over other systems e.g., Vaccinia virus, BCG or Salmonella: (1) immunity to L. monocytogenes is well characterized and known to be exclusively cell-mediated and extremely effective; (2) L. monocytogenes is not a particularly virulent organism except in a few special cases (e.g., pregnant women) and infections caused by L. monocytogenes are treatable with antibiotics; (3) a L. monocytogenes-based vaccine may be administered orally or parenterally; (4) L. monocytogenes has a predilection for macrophages but spreads to and grows in non-professional phagocytic cells; (5) L. monocytogenes grows in the cytoplasm of infected cells inducing a different type of immunity than Salmonella, for example, which resides in the phagolysosome.

Vaccines may be generated against HIV using the disclosure of the present invention to create an expression system in L. monocytogenes in which an HIV antigen is expressed. For example, a fusion protein between the L. monocytogenes LLO protein and the HIV envelope protein, gp120, may be created using PCR technology since the DNA sequences are known. Other HIV antigens that may be used in place of gp120 include, for example, the gag protein or the reverse transcriptase protein.

In addition to vaccines to provide preventative immunity, vaccines may also be generated for post-exposure treatment of HIV infection. Such vaccines include, for example, a recombinant L. monocytogenes genetically engineered to express an HIV antigen, such as rev (reactivation factor) or nef (negative regulatory factor) which may be involved in the reactivation and latency of the virus, respectively. One skilled in the art, once armed with the present disclosure, would also be able to create other vaccines of the present invention targeted against additional HIV antigens.

The DNA encoding the foreign antigen may be inserted, for example, into plasmid pAM401 which contains the L. monocytogenes prfA gene. The plasmid may then be stably integrated into L. monocytogenes, for example, by transfecting the plasmid into a prfA minus mutant of L. monocytogenes. Like the other examples of the invention, it is believed that this fusion protein would be secreted and may generate a cell-mediated immune response upon administration to a patient.

It will be understood by one skilled in the art that the vaccines of the present invention may also be produced, for example, by integrating the DNA encoding the fusion protein into the L. monocytogenes chromosome rather than incorporating it into a plasmid. Further, one skilled in the art, once armed with the present invention, could engineer the recombinant L. monocytogenes vaccine such that the L. monocytogenes is antibiotic-sensitive, for example, so that an infection may be treated with antibiotics.

It will also be understood that the vaccines of the present invention may be used to generate a cell-mediated response against numerous diseases. Numerous DNA sequences are available, for example, through GenBank (Mountain View, Calif.), to provide the necessary information to create fusion proteins directed against a variety of antigens.

What is claimed:

1. A vaccine comprising recombinant *Listeria monocytogenes* that expresses and secretes a fusion protein, the vaccine causing the production of a cytotoxic T-cell response in a vertebrate, wherein said fusion protein comprises a foreign antigen of an infectious agent and Listeriolysin O protein or a foreign antigen of an infectious agent and a signal sequence from a listerial protein.

2. The vaccine of claim 1 wherein the foreign antigen is expressed from a vector.

3. The vaccine of claim 1 wherein the foreign antigen is expressed from the *Listeria monocytogenes* chromosome.

4. The vaccine of claim 1 wherein the foreign antigen comprises an influenza antigen.

5. The vaccine of claim 4 wherein the influenza antigen comprises influenza nucleoprotein.

6. The vaccine of claim 1 wherein the fusion protein comprises Listeriolysin O.

7. The vaccine of claim 1 wherein said fusion protein comprises a signal sequence from Listeriolysin O.

8. A method of eliciting a cytotoxic T-cell response to a selected infection in a vertebrate caused by an infectious agent comprising administering an effective amount of a vaccine according to claim 1 wherein said foreign antigen is an antigen of the infectious agent.

9. The method of claim 8 wherein the antigen comprises a peptide recognized by the cytotoxic T-cells after vaccination, the peptide being the same as an antigenic peptide recognized by an infected vertebrate.

10. The method of claim 8 wherein the antigen is expressed from a vector harbored by said recombinant *Listeria monocytogenes*.

11. The method of claim 8 wherein DNA encoding the antigen is integrated into the *Listeria monocytogenes* chromosome.

12. The method of claim 8 wherein the antigen comprises an influenza antigen.

13. The method of claim 8 wherein the fusion protein expressed and secreted by said recombinant *Listeria monocytogenes* comprises a foreign antigen of an infectious agent and Listeriolysin O protein.

14. The method of claim 13 wherein said fusion protein comprises a signal sequence from Listeriolysin O.

15. A recombinant *Listeria monocytogenes* culture capable of expressing and secreting a fusion protein comprising viable *Listeria monocytogenes* transformed with an expression vehicle containing DNA encoding at least a portion of Listeriolysin O protein in translational reading frame with DNA encoding a foreign antigen of an infectious agent.

* * * * *

UNITED STATES PATENT AND TRADEMARK OFFICE
CERTIFICATE OF CORRECTION

| | |
|---|---|
| PATENT NO. : 5,830,702 | Page 1 of 1 |
| DATED : November 3, 1998 | |
| INVENTOR(S) : Daniel A. Portnoy et al. | |

It is certified that error appears in the above-identified patent and that said Letters Patent is hereby corrected as shown below:

Column 16,
Line 12, "a-modified" should be -- α– modified --.
Line 60, -- µA -- should be -- µl --.

Column 27, claim 1,
Line 18, "fusion protein" should be -- foreign antigen --.
Line 20, "fusion protein" should be -- foreign antigen --.

Signed and Sealed this

Sixth Day of November, 2001

Attest:

NICHOLAS P. GODICI
*Attesting Officer*    *Acting Director of the United States Patent and Trademark Office*